(12) United States Patent
Staddon et al.

(10) Patent No.: US 6,407,058 B1
(45) Date of Patent: Jun. 18, 2002

(54) MODIFYING THE PERMEABILITY OF PHYSIOLOGICAL BARRIERS

(75) Inventors: James Martin Staddon; Mary Louise Morgan, both of London (GB); Marianne Jennifer Ratcliffe, Boston, MA (US)

(73) Assignee: Eisai Co., Limited, Tokyo (JP)

( * ) Notice: Subject to any disclaimer, the term of this patent is extended or adjusted under 35 U.S.C. 154(b) by 0 days.

(21) Appl. No.: 09/280,593

(22) Filed: Mar. 29, 1999

(30) Foreign Application Priority Data

Sep. 30, 1996 (GB) ............................... 9620390

(51) Int. Cl.[7] .......................... A61K 38/00; A61K 31/40
(52) U.S. Cl. ........................................ 514/2; 514/414
(58) Field of Search ..................... 514/2, 414

(56) References Cited

U.S. PATENT DOCUMENTS

| 5,189,046 A | 2/1993 | Burch et al. ................. 514/330 |
| 5,475,511 A | 12/1995 | Hudkins et al. ............ 546/250 |
| 5,519,035 A | 5/1996 | Maiese et al. .............. 514/307 |

FOREIGN PATENT DOCUMENTS

| WO | 9212119 | 7/1992 |
| WO | 9513820 | 5/1995 |
| WO | 9616170 | 5/1996 |
| WO | WO-96/16170 A2 * | 5/1996 |
| WO | 9635417 | 11/1996 |

OTHER PUBLICATIONS

Ratcliffe et al., "Dephosphorylation of the Cadherin–Associated p100/p120 Proteins in Response to Activation of Protein Kinase C in Epithelial Cells", J. of Biol. Chemistry, v. 272, No. 60, pp. 31894–31901 (1997), Issue of Dec. 12.
Laemmli, "Cleavage of Structural Proteins During the Assembly of the Head of Bactriophage T4", Nature, v. 227, pp. 680–685, Issue of Aug. 15, 1970.
Rubin et al., "A Cell Culture Model of the Blood–Brain Barrier ", J. of Cell Biology, v. 115, pp. 1725–1735 (1991).
Staddon et al., "p120, a p120–Related Protein (p100), and the Cadherin/Catenin Complex", J. of Cell Biology, v. 130, No. 2, pp. 369–381, Jul., 1995.
Staddon et al., "Evidence that Tyrosine Phosphorylation May Increase Tight Junction Permeability", J. of Cell Science, v. 108, pp. 609–619, (1995).
Boyle et al., "Phosphopeptide Mapping and Phosphoamino Acid Analysis by Two–Dimensional Separation on Thin–Layer Cellulose Plates", Methods in Enzymology, v. 201, pp. 110–149 (1991)pp. 110–149 (1991).

* cited by examiner

*Primary Examiner*—Dwayne C. Jones
(74) *Attorney, Agent, or Firm*—Hale and Dorr LLP

(57) ABSTRACT

The degree of phosphorylation of serine and threonine residues of p100/p120 can affect the permeability of physiological barriers and also cell—cell adhesion properties. By changing physiological levels, various disorders can be treated, including multiple sclerosis, cancer, head injuries, oedema, stroke, inflammation and gastric ulcers. Furthermore, drugs can be allowed to pass across physiological barriers and the barriers can then be closed.

24 Claims, 19 Drawing Sheets

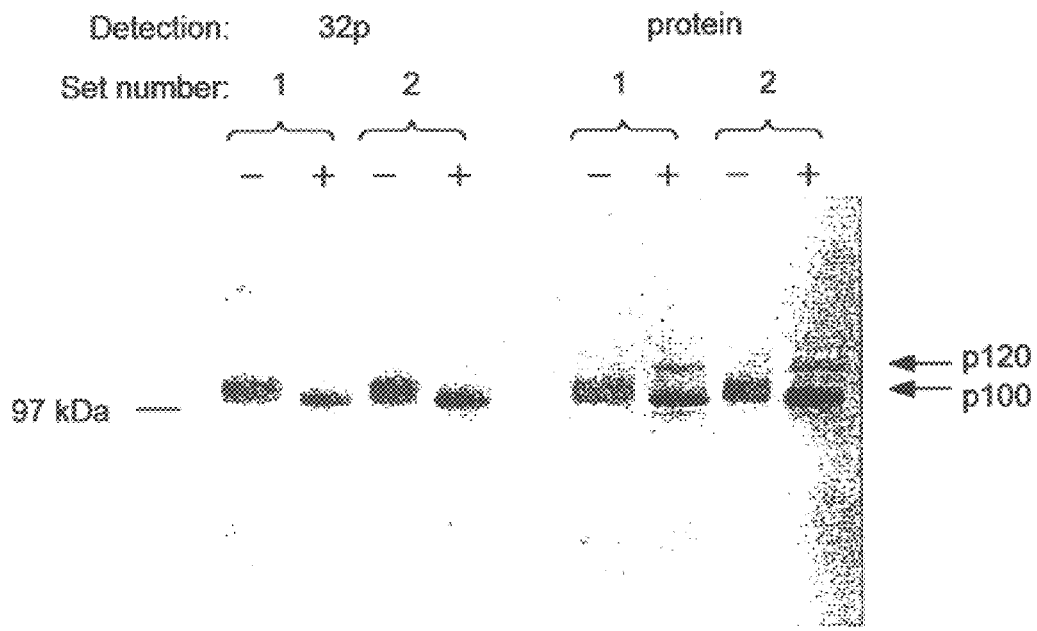
FIG. 7A
| PDB Treatment: | Set 1 | | Set 2 | |
|---|---|---|---|---|
| | − | + | − | + |
| 32p | 1.87 | 0.79 | 1.74 | 1.08 |
| Protein | 1.29 | 0.94 | 1.47 | 1.38 |
| 32P/protein($P_n$) | 1.45 | 0.84 | 1.18 | 0.78 |
| $P_{n(Control)} : P_{n(PDB)}$ | 1 : 0.58 | | 1 : 0.66 | |
FIG. 7B
FIG. 7C

MODIFYING THE PERMEABILITY OF PHYSIOLOGICAL BARRIERS

This application is a 371 of international application number PCT GB/97/02668, filed Sep. 29, 1997, pending which claimed priority to GB 9620390.6, filed Sep. 30, 1996.

The present invention relates to substances which are useful in modifying cell—cell adhesion and in modifying the permeability of physiological barriers.

Cell—cell adhesion is of crucial importance for the development and maintenance of tissue structure. Furthermore, regulation of such adhesion plays a normal role in physiological situations such as tissue turnover. Aberrant control may contribute to the aetiology of pathologies such as cancer and inflammation.

Therefore, there has been considerable interest in the basic processes whereby cells adhere to each other and ways in which such processes may be regulated. In general, cell—cell adhesion involves proteins on neighbouring cells that bind to one another. The cytoplasmic domains of proteins actually involved in adhesion can also physically associate with other cytoplasmic proteins that may either play a mechanical role, such as providing links with other proteins, or provide a regulatory influence.

p120 and p100 are members of the armadillo protein family. The armadillo repeats found in the members of this family appear to provide means whereby proteins can interact with others. p120 and p100, intracellular, cytoplasmic proteins, are now known to associate with cadherins, which are $Ca^{2+}$-dependent adhesion molecules that contribute in an important way to cell—cell adhesion. Cadherins are important in control of cell proliferation. If cadherins fail to function properly, cells can proliferate in an unregulated fashion and metastasize. Cadherins are also thought to be important components in controlling the permeability of physiological barriers i.e. cell tight junctions. Here, disruption of cadherin based cell—cell adhesion leads to increased tight junction permeability. This has raised the possibility that tight junctions, although potentially regulatable in themselves, may be regulated by the adhesiveness of the adherens junction. In turn, cadherin adhesiveness may be regulated by the phosphorylation state of associated catenins, including p100 and p120.

The blood-brain barrier is an important example of a cell tight junction. It serves to separate the molecular, ionic and cellular environment of the blood from that of the brain. To a major degree, this separation is achieved by inter-endothelial tight junctions of high electrical resistance which greatly diminish paracellular flux. It is clear that the permeability of the tight junctions of the blood-brain barrier is not immutable. Rather, permeability appears to undergo dynamic regulation, but the way in which this is achieved is not fully understood.

In WO95/13820 it is disclosed that tyrosine protein phosphorylation is a key regulator of the permeability of tight junctions in both epithelial and endothelial cells; tyrosine protein phosphorylation may therefore be manipulated to control the permeability of the blood-brain and other physiological barriers. Decreasing the degree of tyrosine protein phosphorylation reduces permeability of the blood-brain or other barrier, whereas increasing the degree of tyrosine protein phosphorylation increases permeability. WO95/13820 also disclosed that the proteins p100 and p120 are believed to be substrates of tyrosine kinase. Further information regarding p100 and p120 is provided in WO96/16170.

Although WO95/13820 and WO96/16170 provide important information regarding the functioning of p100 and p120 this information is not complete. Unexpectedly, the present inventors have now discovered that p100 and/or p120 participate in a cycle which involves the phosphorylation/dephosphorylation of serine/threonine residues on these proteins. Furthermore they have shown that this cycle is regulatable by agents which are known tumour promoters, inflammatory mediators and tight junction permeability modulators. Thus, agents which interfere with regulation of this cycle itself or pathways involved in its regulation could have application to a wide variety of medical situations.

According to the present invention there is provided an agent capable of inducing the phosphorylation of serine and/or threonine residues of p100 and/or p120, for use in medicine.

The present invention also provides an agent capable of inducing the dephosphorylation of phosphorylated serine and/or threonine of p100 and/or p120 residues, for use in medicine.

By using an agent as described above, the permeability of physiological barriers i.e. tight junction permeability could be modified and cell—cell adhesion could also be modified.

By way of example, one way of utilising the present invention is to adjust the activity of protein kinase C. The present inventors have found that dephosphorylation of phosphorylated serine and/or threonine residues in p120 and/or p100 can be induced by increasing protein kinase C activity (i.e. by using protein kinase C activators), and that the phosphorylation of serine and/or threonine residues present in p100 and/or p120 can be induced by decreasing protein kinase C activity (i.e. by using protein kinase C inhibitors).

Examples of protein kinase C inhibitors are phorbol diesters, bryostatins 1 and 2, (−) indolactams V and (+) indolactam V, teleocidind, DHI ([6-(N-Decylamino)-4-hydroxymethylindole]) and ADMB ([3-(N-Acetylamino)-5-(N-decyl-N-methylamino)benzyl alcohol]), lipotoxin A4 and B4, mezerein, (−)-7-octylindolactam V, resiniferatoxin, thymeleatoxin. Protein kinase C may also be activated by ligands that bind to receptors to generate diacylglyccrol. Examples of these are bombesin and other neuropeptides, platelet-derived growth factor, epidermal growth factor.

Examples of protein kinase C inhibitors are A3 ([N-(2-Aminoethyl)-5-chloronaphthalene-1-sulfonamide]—this is optionally combined with HCl), bisindolylmaleimide I (also known as GF 109203X), chelerythrine chloride, Gö6976, Gö7874, H-7 ([1-(5-isoquinolinesulfonyl)-2-methylpiperazine]—this is optionally combined with HCl), hypericin, K-252a, b and c, melittin, phloretin, pseudohypericin, rottlerin, Ro 31-8220, Ro 32-0432, LY333531, (−)balanonl. Other examples are givine in "Drug Delivery Today, 1996, vol 1, pp438–447".

The term "protein kinase C", which is sometimes referred to as "PKC", is used herein to refer to a class of enzymes which catalyse the transfer of phosphate from ATP to the serine or threonine residues of polypeptides. Preferably this occurs in a specific manner so that other amino acid residues are not phosphorylated.

Activation of these enzymes can generally be inferred by assaying with MARCKS (a PKC specific substrate). MARCKS is the term used for M̲yristoylated A̲lanine R̲ich C̲ K̲inase S̲ubstrate. This is a protein which was the first major PKC substrate identified. If increased phosphorylation of MARCKS is observed, it can usually be inferred that activation of PKC has occurred.

Inhibitors of PKC can be identified by their ability to prevent or reduce PKC activation.

The present invention is however not limited to the use of activators/inhibitors of PKC since other agents which work independently of PKC but which can affect the level of phosphorylation of threonine and/or serine residues of p100 and/or p120 can be used.

For example, lysophosphatidic acid (LPA) or histamine may be used to induce dephosphorylation of threonine and/or serine residues present in p100 and/or p120 and agents which bind LPA or histamine or blockers of these agents may be used to block the effect of LPA or histamine.

This effect might also be achieved by the use of compositions which are hyperosmolar with respect to the physiological environment proximal to p100 and/or p120 (e.g. hyperosmolar solutions of sugars such as mannitol or arabinose).

Hyperosmotic solutions are believed by some to open up the blood-brain barrier by causing the shrinking of brain endothelial cells which results in the mechanical opening of the endothelial tight junctions. However in view of the information provided herein, it is possible that hyperosmotic treatment triggers intracellular signaling processes leading to p100/p120 dephosphorylation which, as these are junctional proteins, could be responsible for the increase in tight junction permeability.

The present invention is therefore important in indicating that the use of hyperosmolar compositions could be avoided by using other agents to induce dephosphorylation of serine and/or threonine residues present in p100 and/or p120. This is significant since the dangers associated with the use of hyperosmolar solutions can be avoided. (Hyperosmolar solutions such as mannitol solutions are currently used clinically.) These dangers are twofold, firstly there is damage associated with rapid infusion of the hyperosmolar solution via the carotid or vertebral arteries. This includes arterial damage, deep venous thrombosis, pulmonary embolism, granulocytopenia, anaemia, sepsis, hemorrhagic cystitis and interstitial pneumonitis. Secondly, neurologic damage can follow blood-brain barrier opening with hyperosmolar treatment including visual changes, seizures and temporary neurological deterioration.

Other agents useful in the present invention can be identified by screening, as described later.

Particular aspects of the present invention will now be disclosed in greater detail.

Physiological Barrier Permeability

Agents of the present invention may be used to modify the permeability of physiological barriers.

a) Increasing Permeability

For example, agents capable of inducing the dephosphorylation of serine and/or threonine residues present in p100 and/or p120 could be used to open physiological barriers temporarily e.g. by increasing the permeability of tight junctions of both endothelial and epithelial cell barriers. These agents are particularly useful in the case of the blood-brain barrier (an example of an endothelial barrier), since they could allow drugs (i.e. therapeutic agents) which would normally not be able to cross this barrier to reach the brain.

The present invention is not however limited to drug delivery to the brain. It could be used for example in the delivery of drugs to other locations e.g. to tumours (especially peripheral tumours) by loosening endothelial cell barriers.

It could also be used, for example, in nasal delivery of drugs by loosening the nasal epithelial cell barrier. Indeed the present invention could be used for providing drug delivery across endothelial and epithelial cell barriers generally.

Where an agent of the present invention is used to facilitate drug delivery it may be administered together with a drug in a single composition.

Alternatively the agent and the drug may be administered separately. Sequential or simultaneous administration of the agent and the drug may be used.

The present invention is not limited to the use of particular drugs since it can be used to deliver a wide variety of drugs to target sites. However, it is anticipated that among the primary candidates for delivery by means of this aspect of the invention will be: anti-tumour compounds, such as methotrexate, adriamycin and cisplatin; growth factors, such as NGF, BDNF and CNTF, which are used to treat neurodegenerative disease; and neurotransmitter antagonists or agonists which do not penetrate the blood-brain barrier (such as certain NMDA receptor blockers).

Another use of the present invention in increasing the permeability of physiological barriers is in opening pulmonary epithelial cell tight junctions. This can act to dilute the accumulation of mucous present in the lungs. It is also useful in aiding the administration of drugs to the lungs, e.g. where an inhaler is used.

b) Decreasing Permeability

Agents capable of inducing the phosphorylation of unphosphorylated serine and/or threonine residues of p100 and/or p120 could be used to decrease the permeability of physiological barriers. This could be achieved for example by decreasing the permeability of tight junctions of both endothelial and epithelial cell barriers. Such agents could be used, for example, in closing tight junctions after they have been opened or in preventing them from opening. In the case of the blood-brain barrier, it will generally be desirable to use these agents to close cell tight junctions in order to avoid possible damage to the brain after they have been opened to allow a drug to cross this barrier.

It is also desirable to close cell tight junctions in the blood-brain barrier for other purposes. For example this can be done:

a) to block or reduce the entry into the brain of lymphocytes which mediate an immune response (useful in treating multiple sclerosis) or of neutrophils which can damage neuronal cells after stroke;

b) to prevent or reduce the entry of metastatic cancer cells into the brain (useful in treating cancer); and c) to prevent or reduce the risk of brain oedema e.g. following stroke or traumatic head injury (useful in treating head injuries, oedema and stroke).

Cell trafficking across endothelia (such as T cell migration across the blood-brain barrier) and epithelia is believed to occur by several sequential steps. The trafficking cell initially binds to the endothelium or epithelium, at first loosely and then more tightly, migrates to the junctional region and is then believed to migrate through the junction. Clearly, tight junctions must be modulated during this process and it is possible that signalling changes involving p100/p120 serine/threonine phosphorylation may occur and be a necessary part of the transmigration process. Therefore blocking serine/threonine phosphorylation changes in p100 and p120 could block transmigration.

The present invention could also be used to decrease the permeability of other physiological barriers. It could therefore be useful in treating oedema (even if this does not occur in the brain). For example it could be used to treat vasogenic oedema in peripheral tissues by reducing the permeability of the vasculature (e.g. in treating high altitude pulmonary oedema). Reducing the permeability of the vasculature is also useful in preventing or reducing metastases (whether in the brain or elsewhere) by preventing or reducing the ability of tumour cells to exit from the vasculature.

Another use of the present invention in respect of treating tumours is that it could be used to reduce the permeability of leaky junctions of the vasculature supplying solid tumours (i.e. to "tighten" these junctions). This can reduce the uptake of nutrients by such cells.

A further use of the present invention is in treating inflammation. This could be achieved by reducing leukocyte migration to peripheral tissues through endothelial cell tight junctions. By reducing the permeability of such junctions leukocyte migration to peripheral tissues can be reduced. The present invention is not however limited to treating inflammation of peripheral tissues. It could be used to treat other inflammatory conditions. For example, it could be used to treat intestinal inflammation. Neutrophil migration across intestinal epithelia can be a cause of intestinal inflammation. By reducing the permeability of epithelial cell junctions intestinal inflammation could therefore be reduced.

A yet further use of the present invention is in treating gastric ulcers. Gastric ulcers can be exacerbated by "loose" tight junctions. Thus decreasing the permeability of tight junctions of gastric epithelial cells could be used in the alleviation of gastric ulcers.

From the foregoing passages it is clear that the present invention could be used to treat a wide variety of different disorders by reducing the permeability of cell junctions in order to prevent cells which can cause disorders from reaching sites where such disorders can arise. The present invention could therefore generally be useful in preventing or reducing aberrant cell trafficking.

Cell—Cell Adhesion Properties

Agents of the present invention could also be used to modify cell—cell adhesion.

For example, such agents could be used to induce the phosphorylation of serine and/or threonine residues of p120 and/or p100 in order to increase the tendency of cells to adhere to one another.

This could, for example, prevent or slow down the loss of contact inhibition which is seen in the development of cancerous cells. Thus the loss of growth control which is associated with loss of contact inhibition could be prevented or reduced. Such agents could also prevent or slow down the increased cell motility, migration and metastasis, which occurs in the development of cancers.

Medicaments

The agents of the present invention (which could modify the permeability of physiological barriers and which could modify cell—cell adhesion properties) could be used in the preparation of medicaments for use in human or in veterinary medicine.

These medicaments could be used for the treatment of an existing condition or for prophylactic treatment and the word "treatment" is used herein to cover both of these alternatives.

An agent for use in the present invention may be combined with a pharmaceutically acceptable carrier to form a pharmaceutically acceptable composition. This pharmaceutical composition will usually be sterile. It may be in any suitable form (depending upon the desired method of administering it to a patient). For example, it may be provided in unit dosage or multiple dosage form. It may be provided as a derivative. Thus pharmaceutically acceptable salts, esters or other derivative forms may be used, provided that activity is retained.

Pharmaceutical compositions within the scope of the present invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with a carrier under sterile conditions.

Screens

Without being bound by theory, a possible scheme is shown in FIG. 1, which will be described later.

In any event the present inventors have established that regulation of the degree of phosphorylation of serine/threonine present in p120/p100 could be used to modify the permeability of physiological barriers and also to modify cell—cell adhesion properties. This finding was not predictable prior to the present invention and is significant in establishing the important regulatory role of p100/p120.

p100 and p120 are described in greater detail in WO95/13820 and WO96/16170, where tyrosine phosphorylation is also discussed. They are proteins with molecular weights of about 100 kDa and about 120 kDa respectively, and are associated with cadherin and cadherin complexes present in endothelial and epithelial cells.

In view of this important finding, the present invention could be used to provide a screen for pharmaceutically active compounds.

For example, p100 and/or p120 could be used to screen for substances capable of increasing the permeability of physiological barriers/reducing cell—cell adhesion. This could be done by screening for substances which can induce the dephosphorylation of phosphorylated threonine and/or serine residues present in p100 and/or p120 (preferably under physiological conditions).

Alternatively p100 and/or p120 could be used to screen for substances capable of decreasing the permeability of physiological barriers/increasing cell—cell adhesion. This could be done by screening for substances which can induce the phosphorylation of threonine and/or serine residues present in p100 and/or p120.

Research Uses

The agents disclosed herein are not limited to being used in medical treatment or in screening since they are generally useful for research into cell—cell adhesion and into physiological barriers (e.g. cell junctions, such as cell tight junctions). In particular, these agents are useful for studying the proteins p100 and p120 and for developing more accurate models of the functions of these proteins. The agents disclosed herein are especially useful in investigating the effects induced by phosphorylation/dephosphorylation of threonine and/or serine residues present in p100 and/or p120.

Diagnostic Uses

Agents of the present invention may be used in diagnosis since they can be used to alter the permeability of physiological barriers in order to allow substances which are useful in aiding a diagnosis to reach a desired location. This may be a location which they would not otherwise reach via a particular route of administration. Thus, for example, substances useful in diagnosis which do not normally cross the blood-brain barrier may be allowed to cross this barrier via the present invention. The present invention can also be used to facilitate the entry of diagnostic substances into tumours.

Any suitable diagnostic substances may be used. Antibodies, antibody fragments, lectins or other molecules having high binding specificity may be linked to diagnostic substances in order to target them to a desired site. (Such molecules can also be linked to drugs to target pharmaceutically active substances to a desired site.) For example cancer cells can be targeted.

Preferred diagnostic substances are useful in imaging. For example, they may be useful in providing brain scans.

In the foregoing discussions, references to "increasing" or "decreasing" the permeability of physiological barriers and to "increasing" or "decreasing" cell—cell adhesion are made in the context of administering agents of the present invention to a patient. These shall be taken to include not only absolute increases/decreases in permeability or adhesion but also the increases/decreases in permeability or adhesion relative to the situation which would arise if a patient were left untreated (rather than being treated with an agent for use in the present invention).

BRIEF DESCRIPTION OF THE DRAWINGS

The present invention will now be described by way of illustration only, with reference to the accompanying figures.

Figure 1:
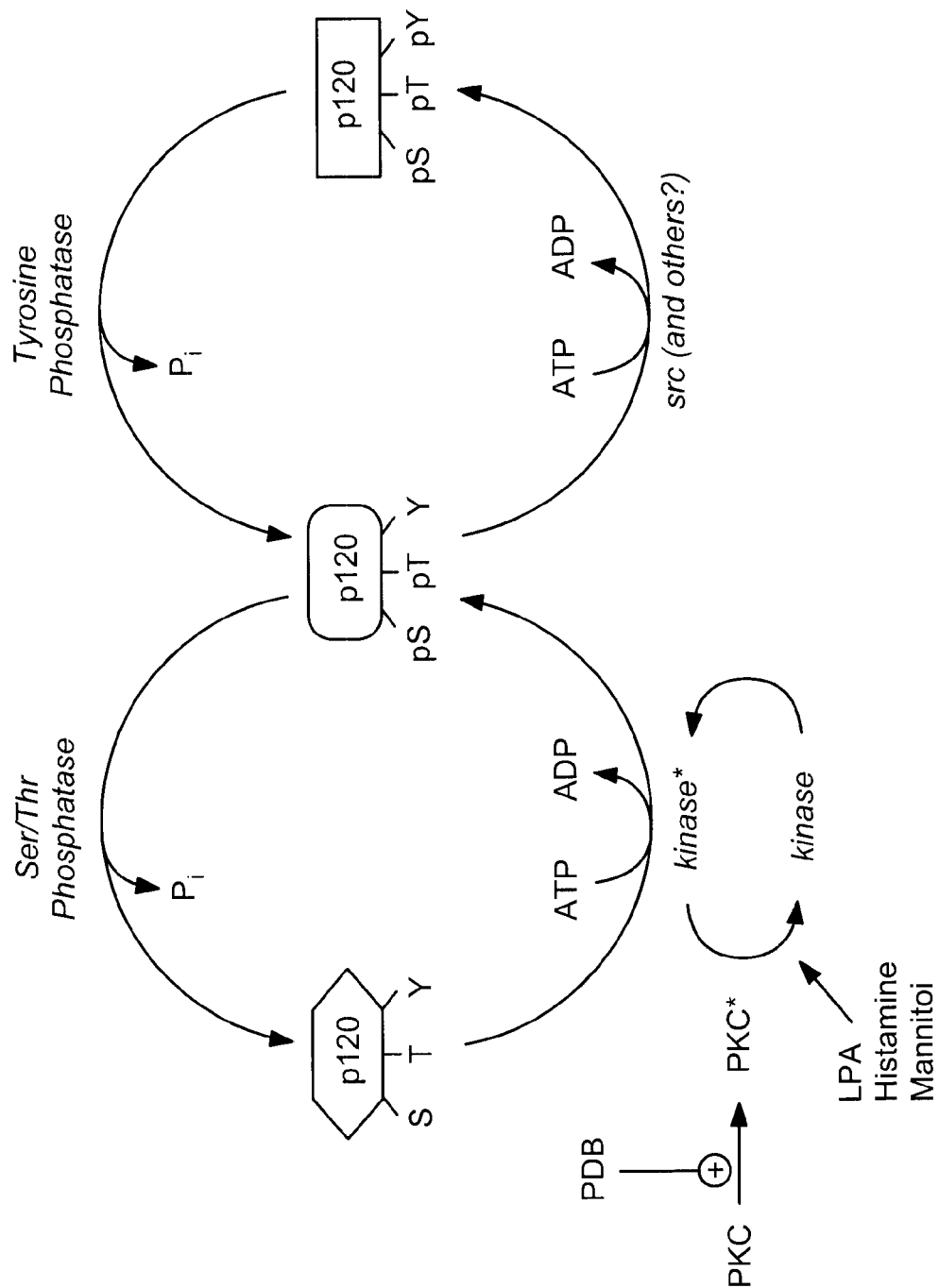
FIG. 1
Figure 2A:
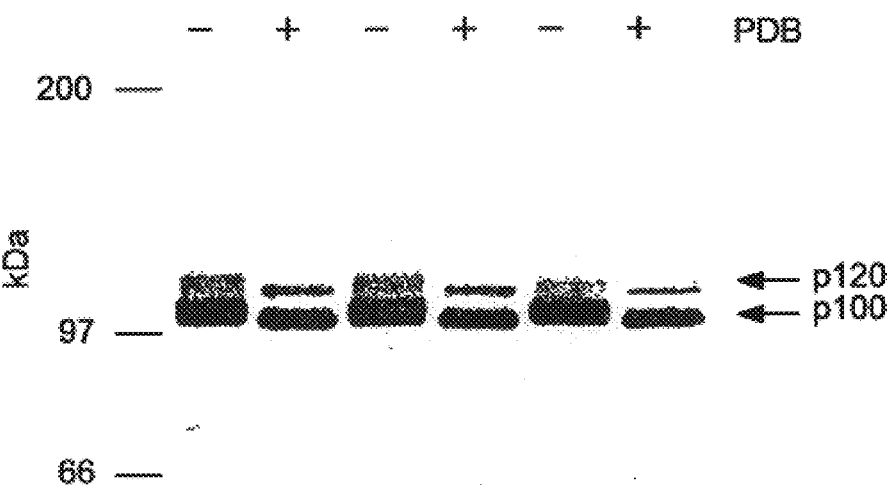
Figure 2B:
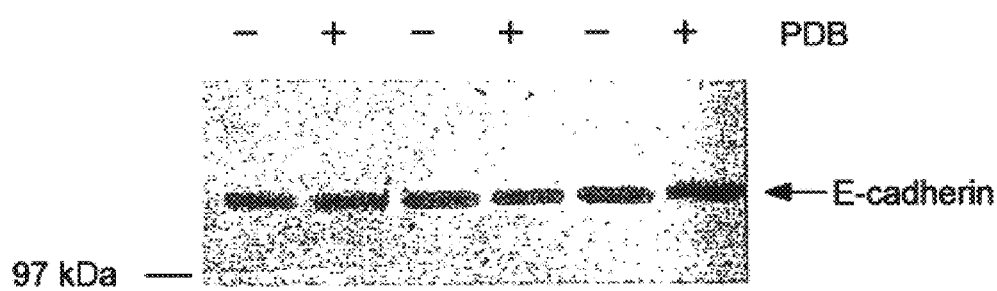
Figure 2C:
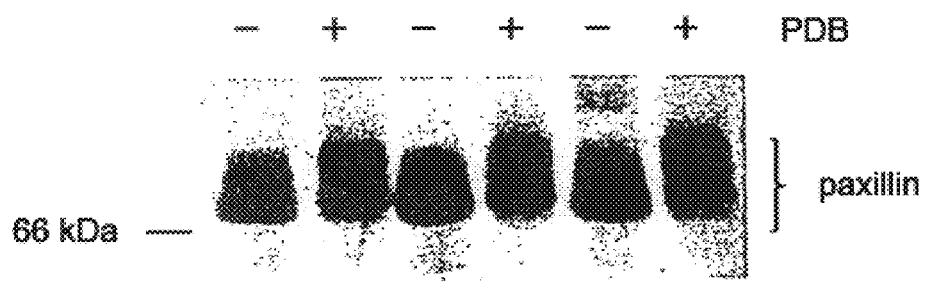
Figure 3:
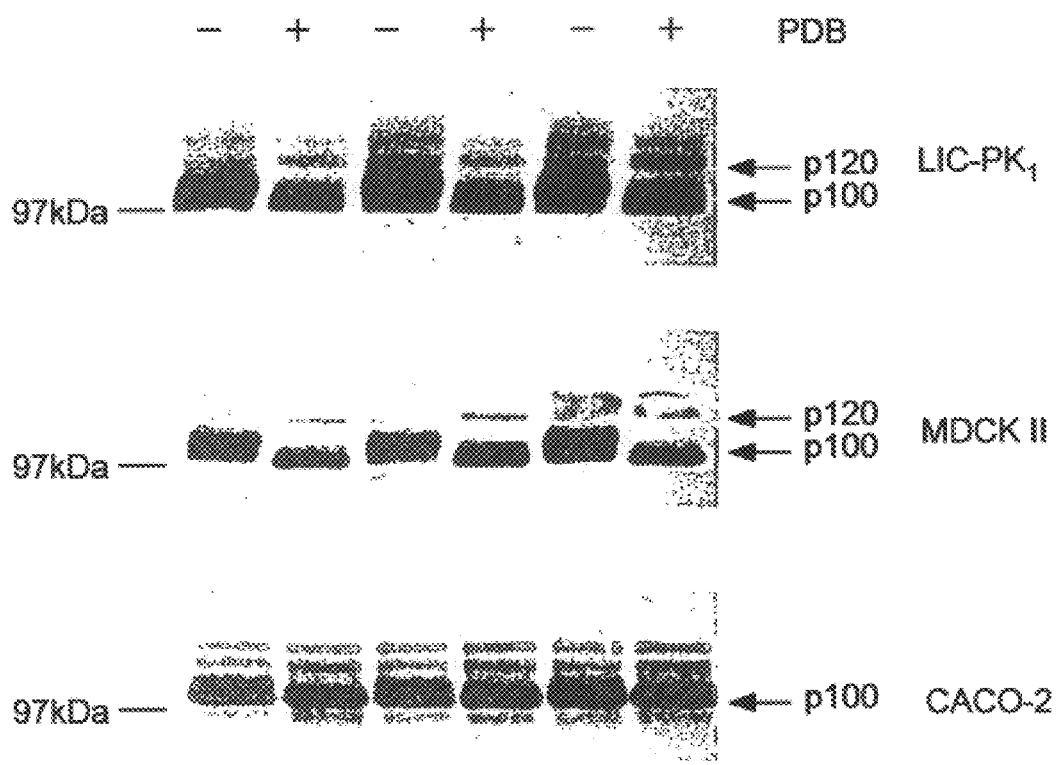
Figure 4:
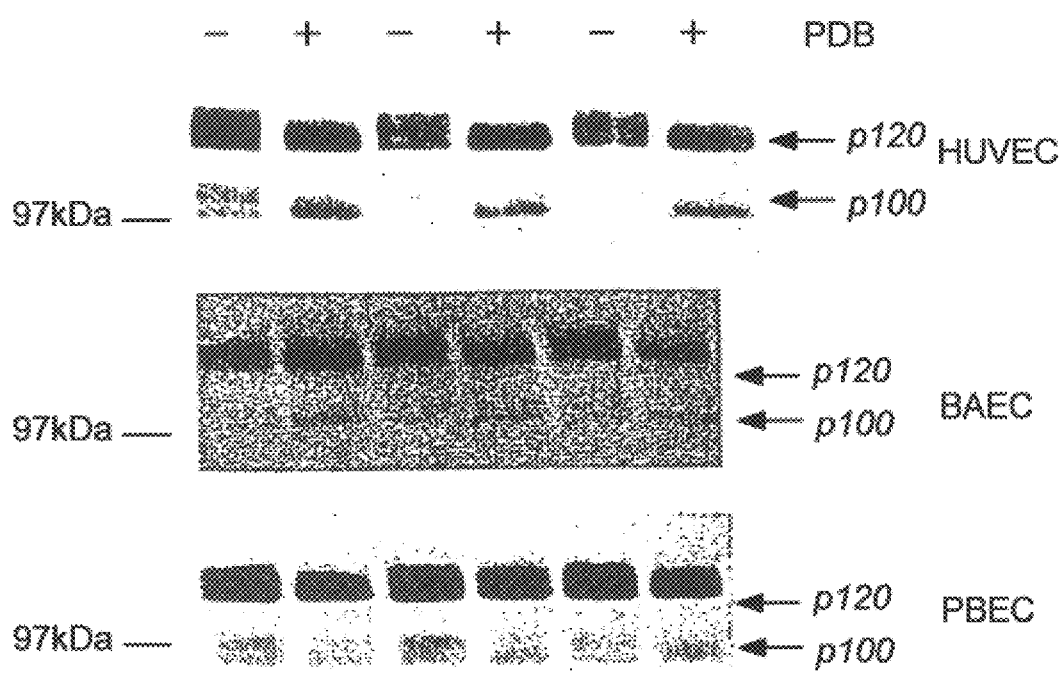
Figures 5A, 5B, 5C, 5D:
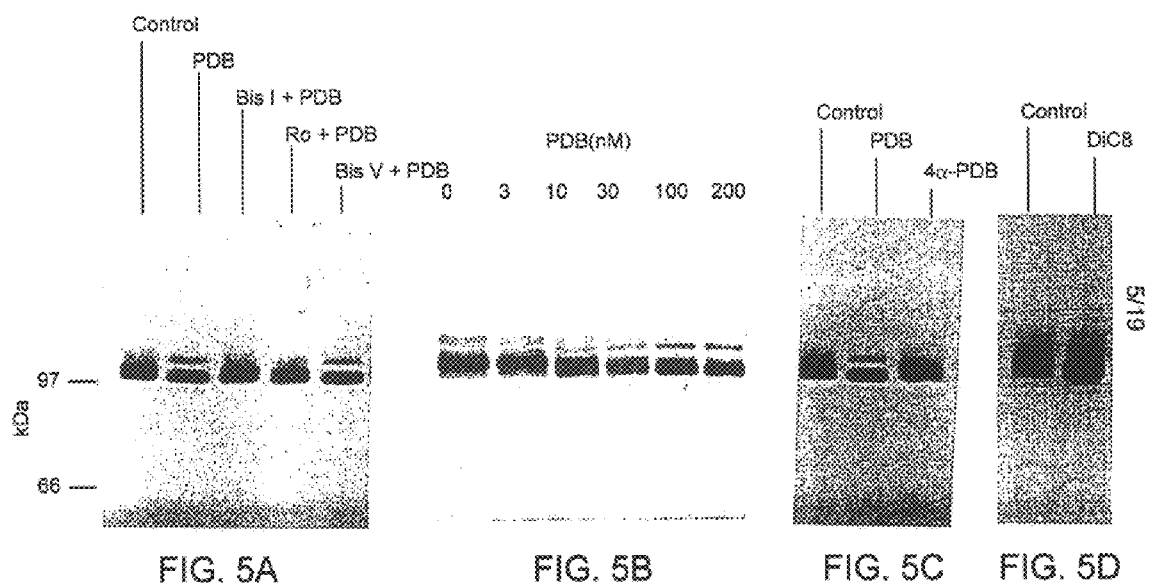
Figure 6:
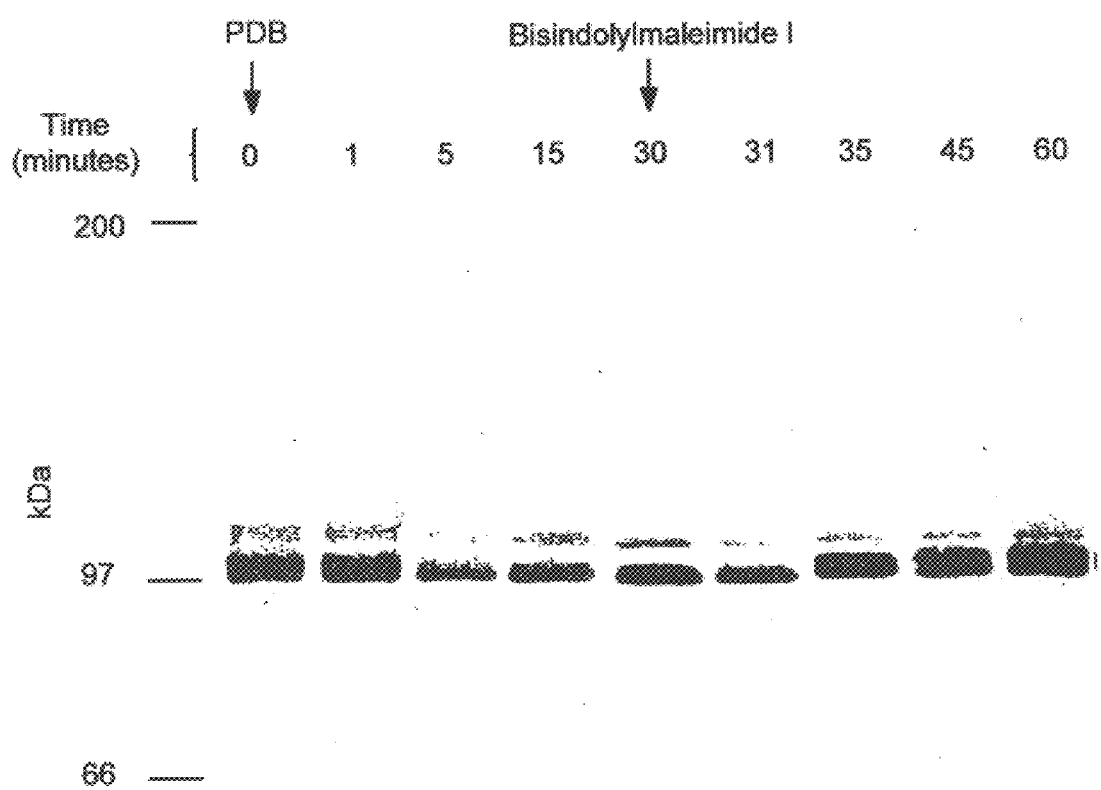

This shows a scheme of how protein kinase C (PKC) activation could result in dephosphorylation of p100 and p120. In order to bring about dephosphorylation of p100/p120, PKC activation, as elicited by phorbol 12,13-dibutyrate (PDB) must lead to net kinase inhibition and/or activation of phosphatases. Activated kinase is depicted as "kinase*". Since the effect on p100/p120 is rapid, and can easily be reversed, it is clear that p100/p120 is capable of cycling between phosphorylated and lesser phosphorylated forms, subject to the action of p100/p120 kinase(s) and p100/p120 phosphatase(s). In resting cells, p120* is phosphorylated on serine and threonine, the level of phosphate being maintained by the opposing actions of a serine/threonine phosphatase, and corresponding kinase. PKC may act directly, or indirectly to inhibit the kinase, leading to p120 dephosphorylation (as represented here). Alternatively, PKC could somehow promote the action of the serine/threonine phosphatase, which would also cause dephosphorylation of p120. This contrasts with the tyrosine phosphorylation cycle of p120; in resting cells there is little or no tyrosine phosphorylation of p100/p120. Following activation of src, or perhaps other related kinases, p120 becomes phosphorylated on tyrosine. In endothelial cells, lysophosphatidic acid (LPA), histamine and mannitol treatment also cause p100/p120 dephosphorylation but, based on experiments using protein kinase C inhibitors, seem to act independently of protein kinase C.

NB: This scheme can also apply to p100, but for simplicity only p120 has been shown.

FIG. 2

The migration of the cellular proteins p100 and p120 during electrophoresis is increased following PDB-treatment of MDCK I cells. PDB (phorbol-12,13-dibutyrate) is a pharmacological activator of protein kinase C. MDCK I cells are a kidney derived epithelial cell line, with particularly well developed junctional complexes. Cells treated for 30 minutes with either 200 nM PDB (+) or vehicle (−) were then lysed into Laemmli sample buffer, and separated by electrophoresis using 6% acrylamide gels. Proteins were transferred to nitrocellulose and probed with antibodies to p100/p120, and then reprobed with E-cadherin and paxillin antibodies. PDB treatment causes p100 and p120 to migrate as faster, tighter bands (A). In contrast, PDB treatment has no effect on E-cadherin (B), and induces an upward band shift of paxillin (C) due to its phosphorylation.

FIG. 3 p100 and p120 electrophoretic mobility is affected by PDB in a number of different epithelial cell lines. LLC-PK$_1$, (a porcine kidney cell line), MDCK strain II cells and gut-derived Caco-2 cells were treated with or without 200 nM PDB for 30 minutes, lysed into Laemmli sample buffer, separated by electrophoresis and analysed by immunoblotting. Migration of p100 and p120 from LLC-PK$_1$ and MDCK II cells increased markedly in response to phorbol ester. The effect was less striking, but still present, in Caco-2 cells.

FIG. 4

The mobility of p100 and p120 during electrophoresis is also altered by PDB-treatment in endothelial cells. The p100/p120 proteins from human umbilical vein endothelial cells (HUVECs), bovine aortic endothelial cells (BAECs) and primary pig brain endothelial cells (PBECs) were all affected by PDB-treatment. Cells were treated with or without 200 nM PDB for 30 minutes, lysed into Laemmli sample buffer, separated by electrophoresis and analysed by immunoblotting with antibodies recognising p100 and p120. In all cases, the mobility of p100 and p120 increased. Thus the effect of PKC activation (via PDB) on p100/p120 mobility is a widespread phenomenon.

FIGS. 5(A–D)

Pretreatment of MDCK I cells with the specific PKC inhibitors bisindolylmaleimide I or Ro 31-8425 for 5 minutes prior to PDB addition completely abolished the p100/p120 band shift (Example 4A). An inactive member of the bisindolylmaleimide class, bisindolylmaleimide V, was unable to block the PDB-induced band shift. Analysis of dose-dependence showed that PDB was effective at concentrations between 30 and 100 nM (Example 4B), corresponding to the concentrations required to activate PKC. Also, an inactive stereoisomer of PDB, 4α-PDB, had no effect on p100/p120 mobility (Example 4C). The effect of PDB could also be obtained by a cell permeant diacylglycerol analogue, 1,2-dioctanoylglycerol (DiC$_8$) (Example 4D). These results demonstrate that the p100/p120 band shift occurs as a response to PKC activation by PDB. This rules out the possibility that the p100/p120 mobility shift seen in response to PDB was due to activation (by PDB) of some unknown pathway. Experimental details: A. MDCK I cells were pretreated with either bisindolylmaleimide I (2.5 μM), an inactive analogue of bisindolylmaleimide I, bisindolylmaleimide V (2.5 μM) or Ro 31-8425 (5 μM) for 5 minutes, and then exposed to 200 nM PDB for 30 minutes. Cell lysates were analysed by electrophoresis, and immunoblotted with p100/p120 antibodies. B. PDB Dose dependence. MDCK I cells were incubated with a range of PDB concentrations from 1 to 200 nM for 30 minutes. p100/p120 mobility increased with increasing PDB concentration, with maximal affect at 100 nM PDB. C. A stereoisomer of PDB, 4α-PDB does not activate PKC, and has no effect of p100/p120 mobility. 4α-PDB was added at 200 nM for 30 minutes. D. DiC$_8$, a cell permeant diacylglycerol analogue induces a p100/p120 mobility shift. MDCK I cells were treated with 0.5 mM DiC$_8$ for 10 minutes.

FIG. 6

Time dependence and reversibility of PDB effect. MDCK I cells were treated with 200 nM PDB for the times indicated, then lysed into Laemmli sample buffer, separated by electrophoresis, and immunoblotted. Reversibility was demonstrated by treating cells with 200 nM PDB for 30 minutes, then adding 2.5 μM bisindolylmaleimide I to inhibit PKC (still in the presence of PDB) for the times indicated. Maximal effect of PDB on p100/p120 in seen between 1 and 5 minutes, and can be reversed by bisindolylmaleimide I with equal rapidity. Addition of the inactive bisindolylmaleimide V did not reverse the p100/p120 band shift (data not shown). These data show that interconversion of p100 and p120 from slower to faster migrating forms is dynamic, and clearly argues against the possibility that the increased p100/p120 mobility is due to proteolysis.

FIGS. 7(A–C)

PDB induces dephosphorylation of p100 and p120. We investigated the possibility that the altered pattern of migration during electrophoresis of p100 and p120 following treatment with PDB is due to a change in the phosphorylation state of these proteins. MDCK I cells were metabolically labelled with [$^{32}$P]orthophosphate, treated with or without 200 nM PDB, and the p100 and p120 isolated by immunoprecipitation with antibodies recognising p100 and p120. This immunoprecipitation was carried out under buffer conditions which removed any associated proteins from p100 and p120. Protein was separated by electrophoresis, transferred to nitrocellulose filters, and exposed to film (Example 6A). The greater the amount of radioactive phosphate incorporated into the protein, the greater the signal on the film. Thus, the level of phosphate present in p100 and p120 from untreated cells could be compared to that from PDB-treated cells by densitometric scanning of the resulting autoradiograph. To normalise for slight differences in protein loading, the same filters were then probed with p100/p120 antibody, and the level of p100/p120 protein determined by densitometry. Thus, the amount of phosphate per unit protein could be calculated. Panel B shows the results of the scanning of the autoradiographs shown in panel A, (arbitrary units). '$P_n$' indicates 'phosphate level normalised for protein'. In this experiment, approximately 40% of the phosphate in p100/p120 was lost following PDB treatment. The results from seven independent sets of such experiments showed that, following PDB treatment, phosphate content of p100/p120 was reduced to 58±11% (mean±s.d.) of that in untreated cells. The dephosphorylation of p100 and p120 is specific, since there was no change in the phosphorylation of E-cadherin immunoprecipitated from the same cell lysates, or on the phosphorylation state of proteins in whole cell extracts (data not shown). This rules out the extremely unlikely possibility that the effect on p100/p120 was an artefact due to non-specific effects of PDB on labelling.

Panel C, shows analysis of the phosphoamino acid (PAA) content of p100/p120. Following phosphate labelling, immunoprecipitation and visualisation of p100/p120 as in panel A above, the levels of p100/p120 protein were determined by immunoblotting. Thus it could be ascertained that approximately equal amounts of protein from PDB-treated and untreated cells were used for the PAA analysis. The p100/p120 bands were excised, and the proteins hydrolysed into their constituent amino acids by boiling in 5.7 M HCl. PAAs were then separated by two-dimensional electrophoresis, and detected by autoradiography. p100/p120 from control cells contains mainly phosphoserine (S), some phosphothreonine (T) and no detectable phosphotyrosine (Y). Following PDB treatment, both phosphoserine and phosphothreonine levels are reduced. Densitometric scanning of the autoradiographs of the PAA analysis revealed a reduction in phosphate signal of approximately 40% (data not shown), agreeing with the values obtained from the whole protein phosphate labelling experiments.

Figure 8A:
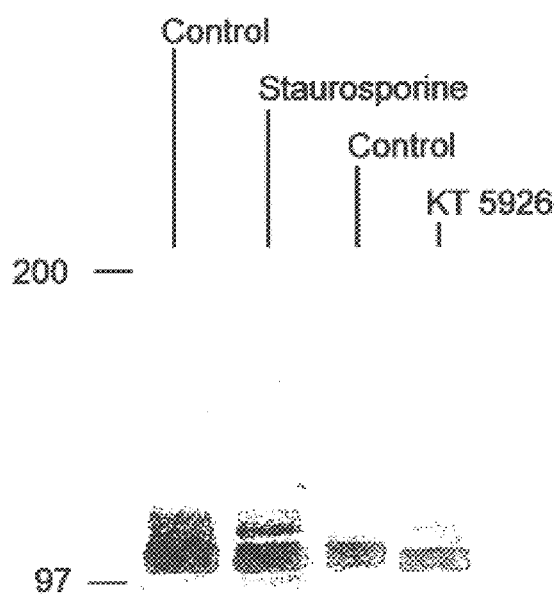
Figure 8B:
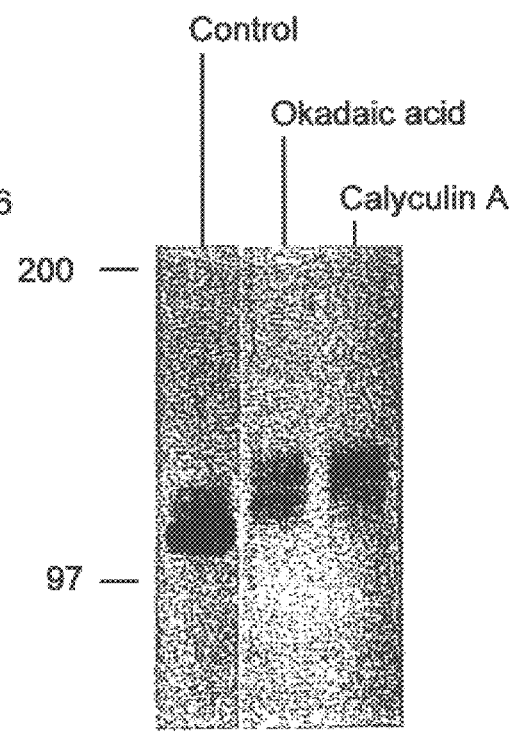

FIGS. 8A and 8B

In order to test the hypothesis that a cycle of p100/p120 dephosphorylation exists MDCK I cells were treated with kinase or phosphatase inhibitors to try and perturb this cycle. Thus, incubation for 60 minutes with 100 nM staurosporine, a broad range kinase inhibitor, induced a p100/p120 band shift similar to that seen in response to PDB (panel A). This would be consistent with inhibition of a p100/p120 kinase. Addition of a more specific staurosporine derivative, KT 5926 (at a concentration of 1 μM) also induced a p100/p120 band shift (panel A), suggesting these inhibitors may indeed act directly on the p100/p120 kinase.

Addition of the serine/threonine phosphatase inhibitors calyculin A (100 nM) or okadaic acid (1 μM) to MDCK I cells from 60 minutes had the opposite effect of p100/p120 mobility; induction of an upward band shift, consistent with increased phosphorylation (panel B). Thus it would appear that in resting cells, a certain level of p100/p120 phosphorylation is maintained by a balance of the opposing effects of kinase and phosphatase. Inhibition of the kinase tips the balance in favour of the phosphatase, causing net p100/p120 dephosphorylation. In contrast, inhibition of the phosphatase leads to predominant kinase activity, manifested by hyperphosphorylation of p100/p120 (see Example 1). We propose that PKC acts to perturb this cycle, perhaps by phosphorylating and inhibiting a p100/p120 kinase. Alternatively, PKC could act to increase the activity of the p100/p120 phosphatase.

Figure 9A:
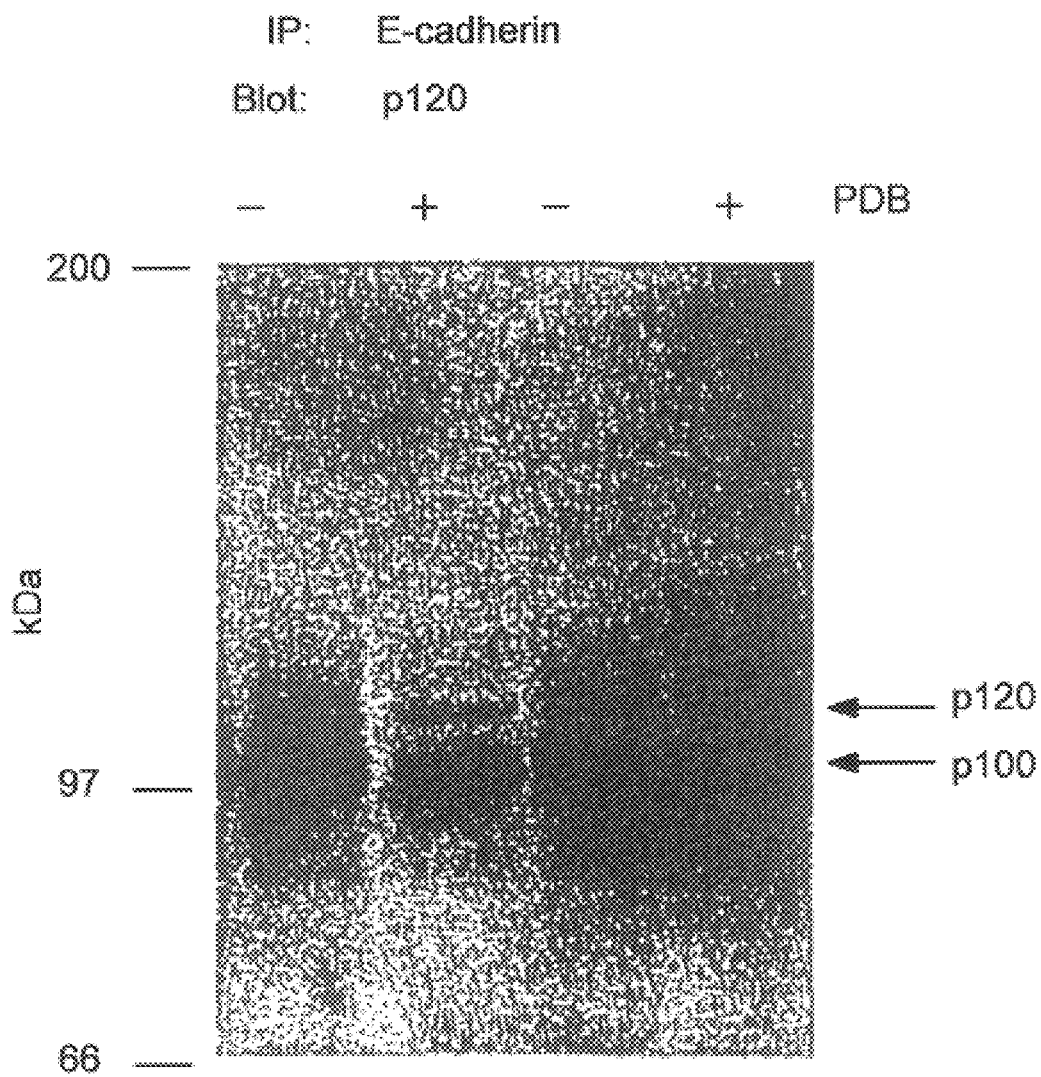
Figure 9B:
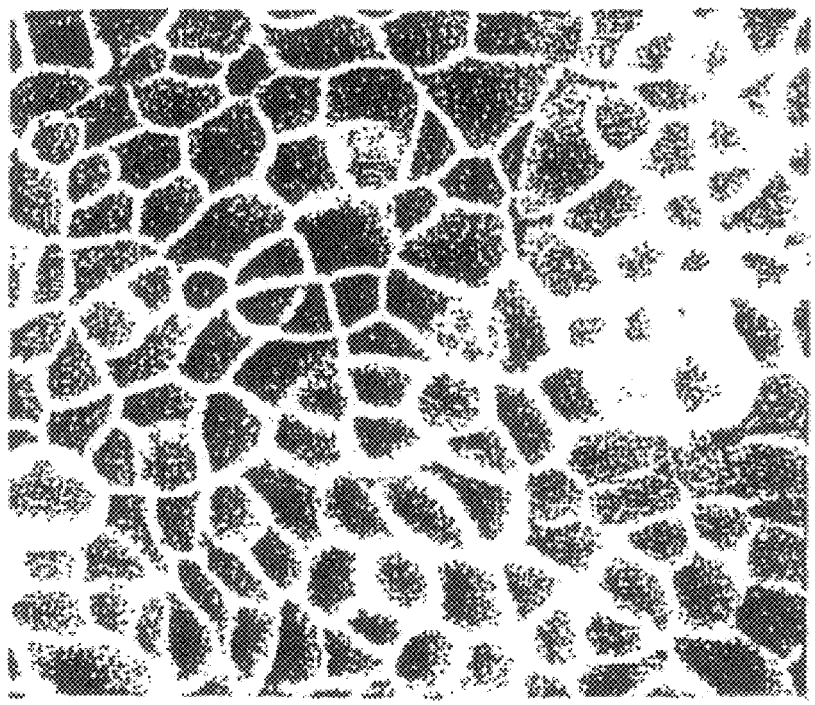
Figure 9C:
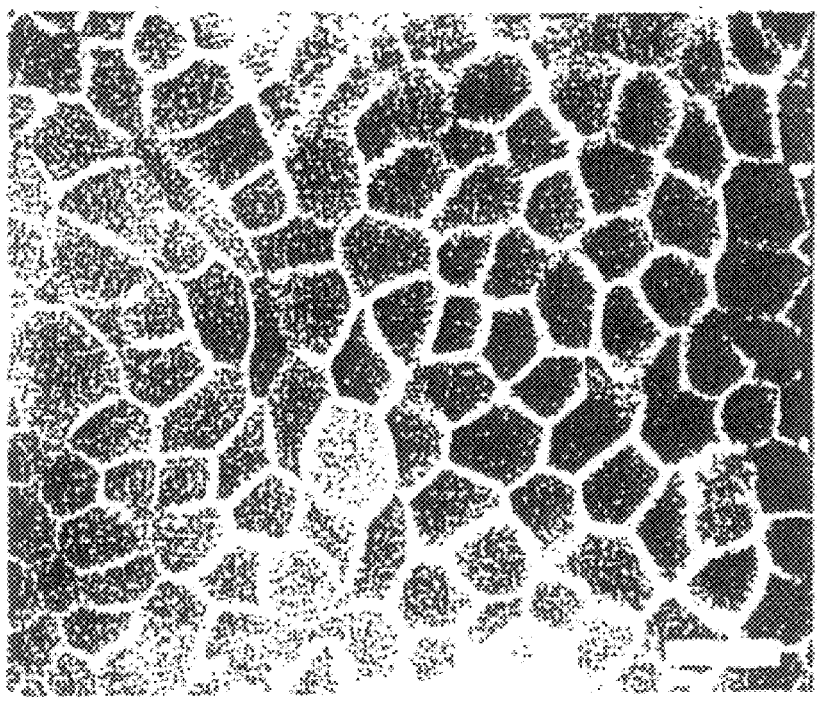
Figure 10:
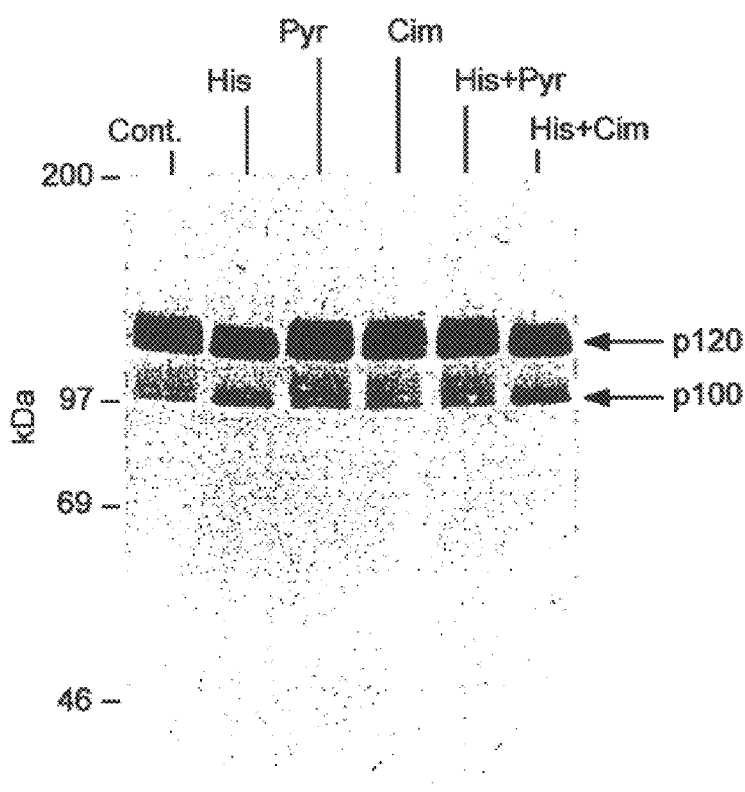
Figure 11:
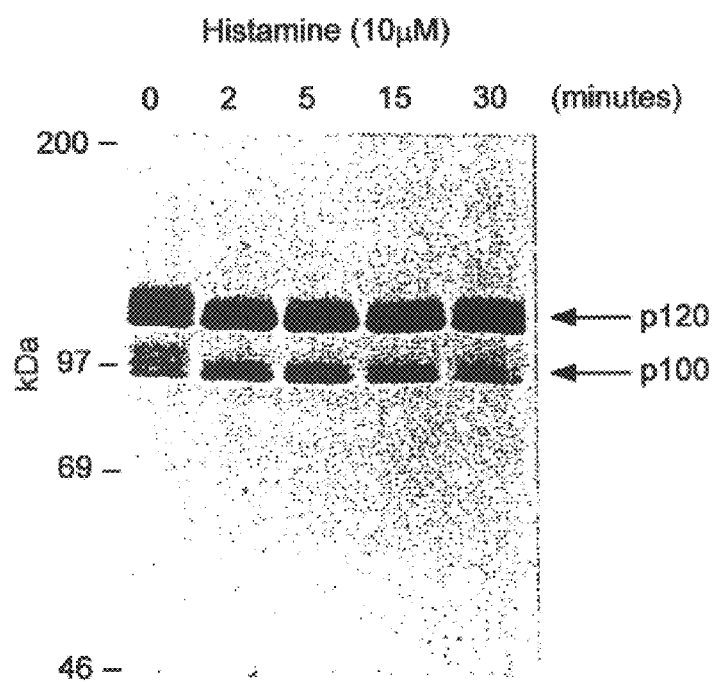
Figure 12:
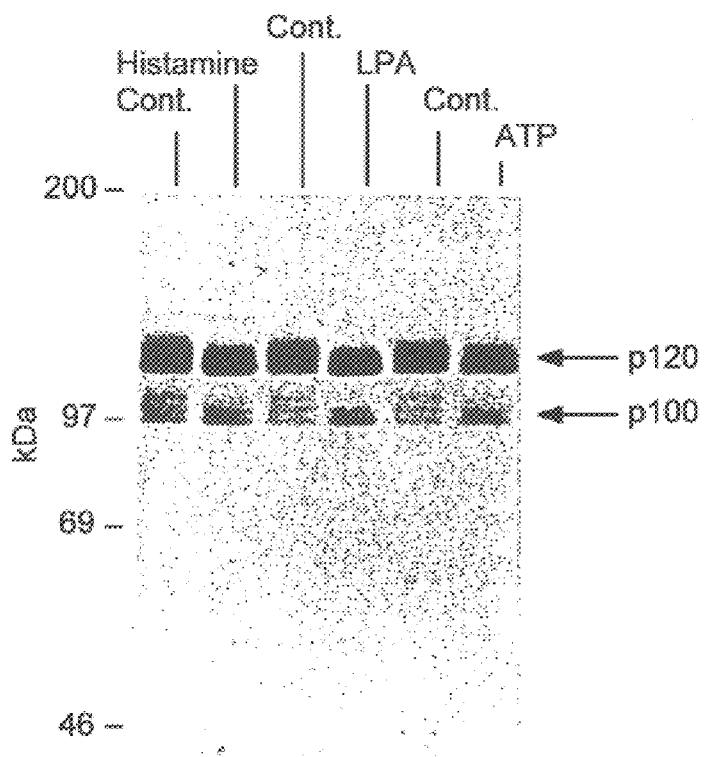
Figure 13:
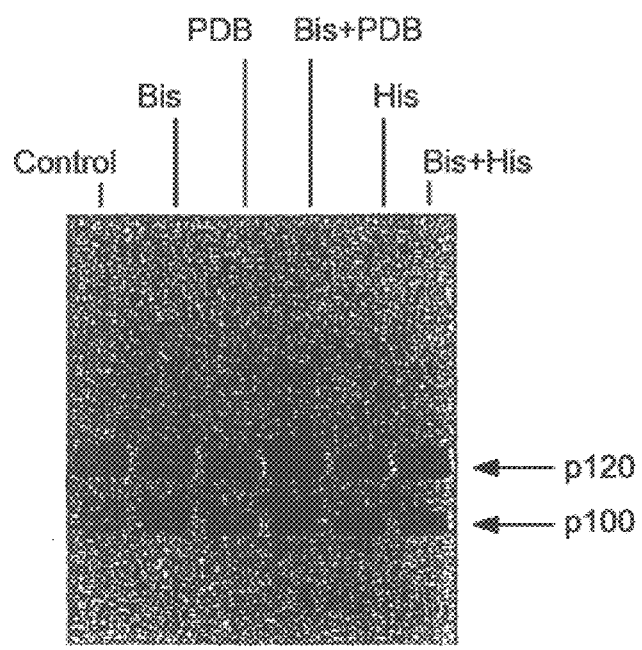
Figure 14:
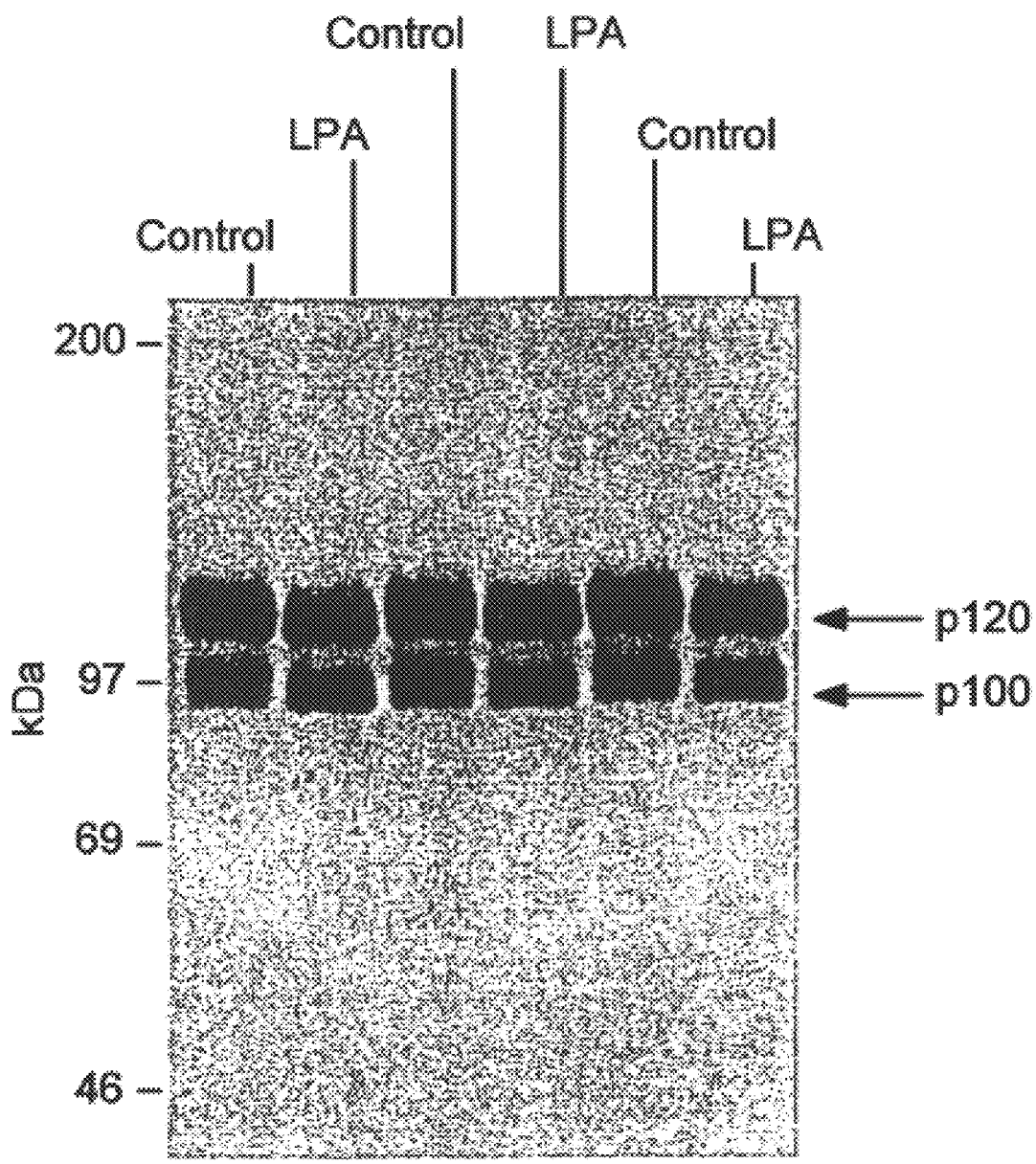
Figure 15:
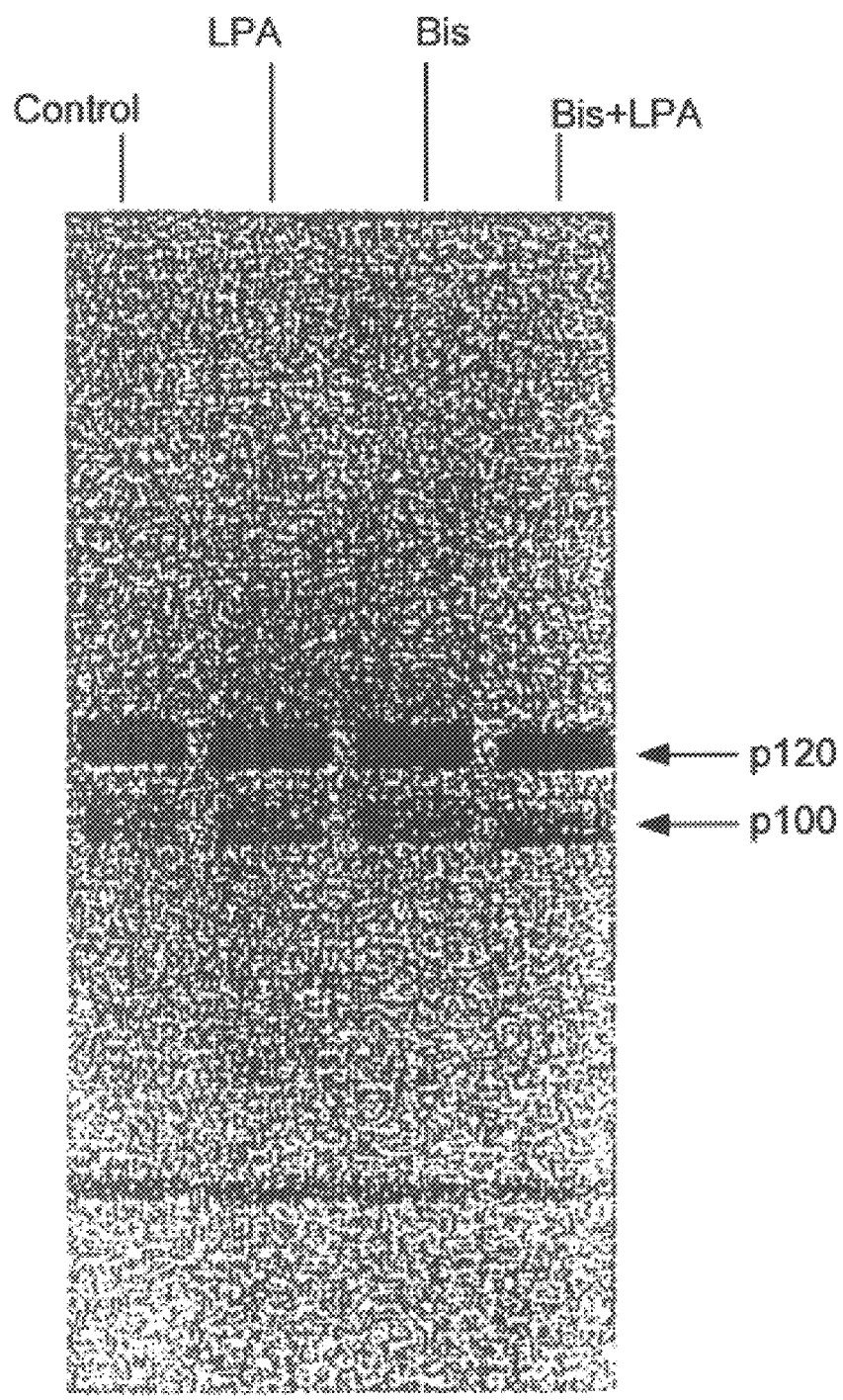
Figure 16A:
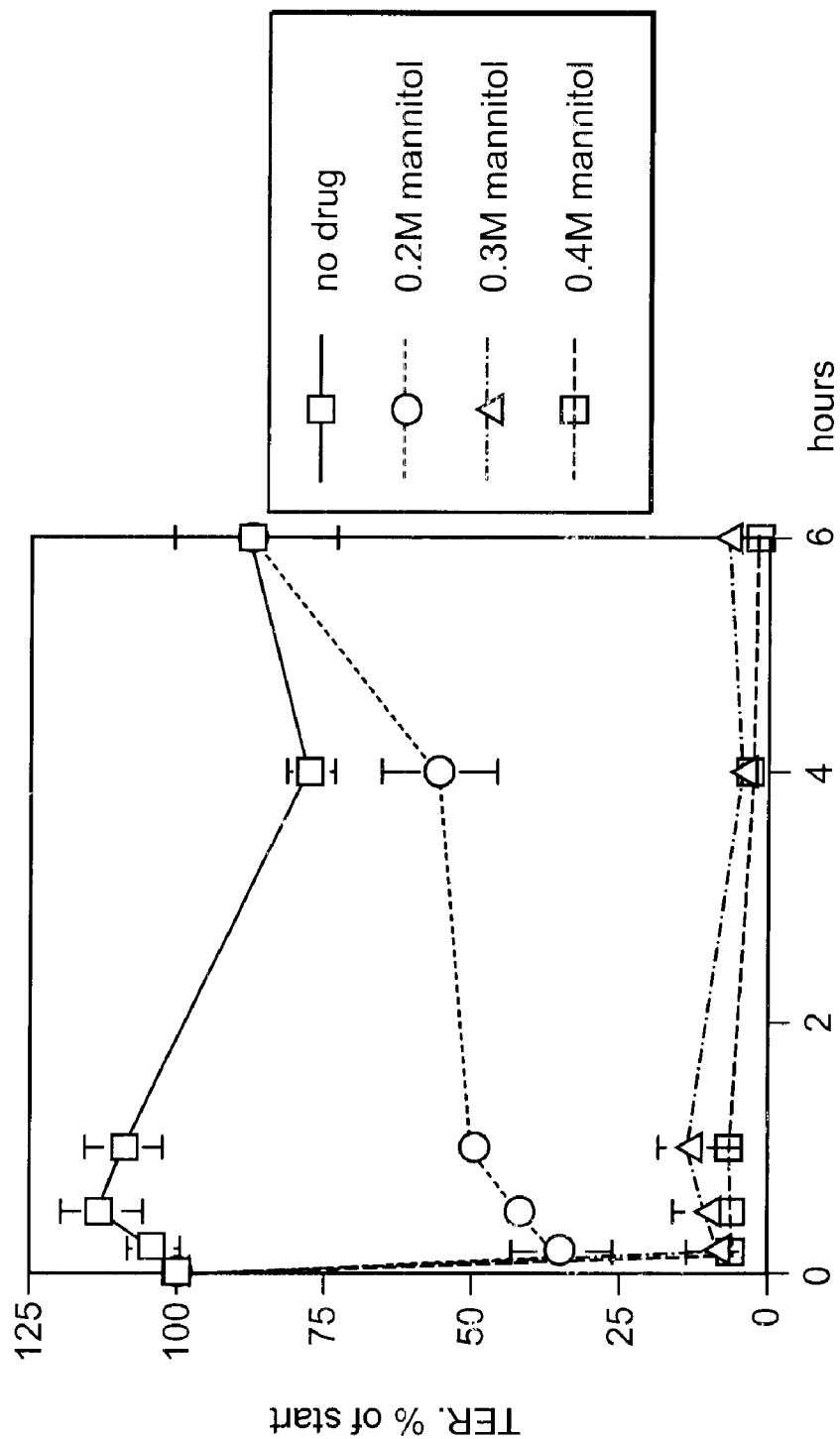
Figure 16B:
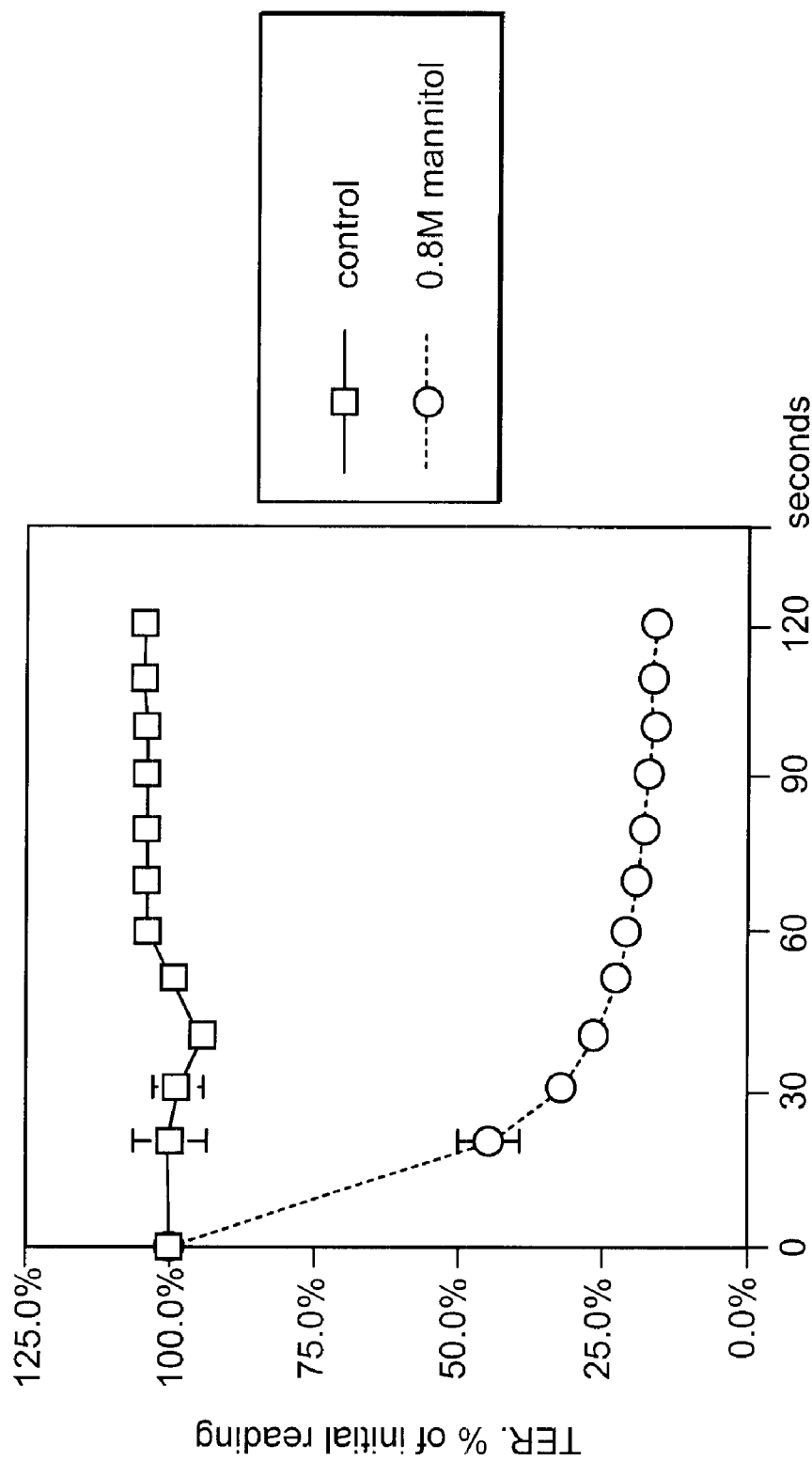
Figure 16C:
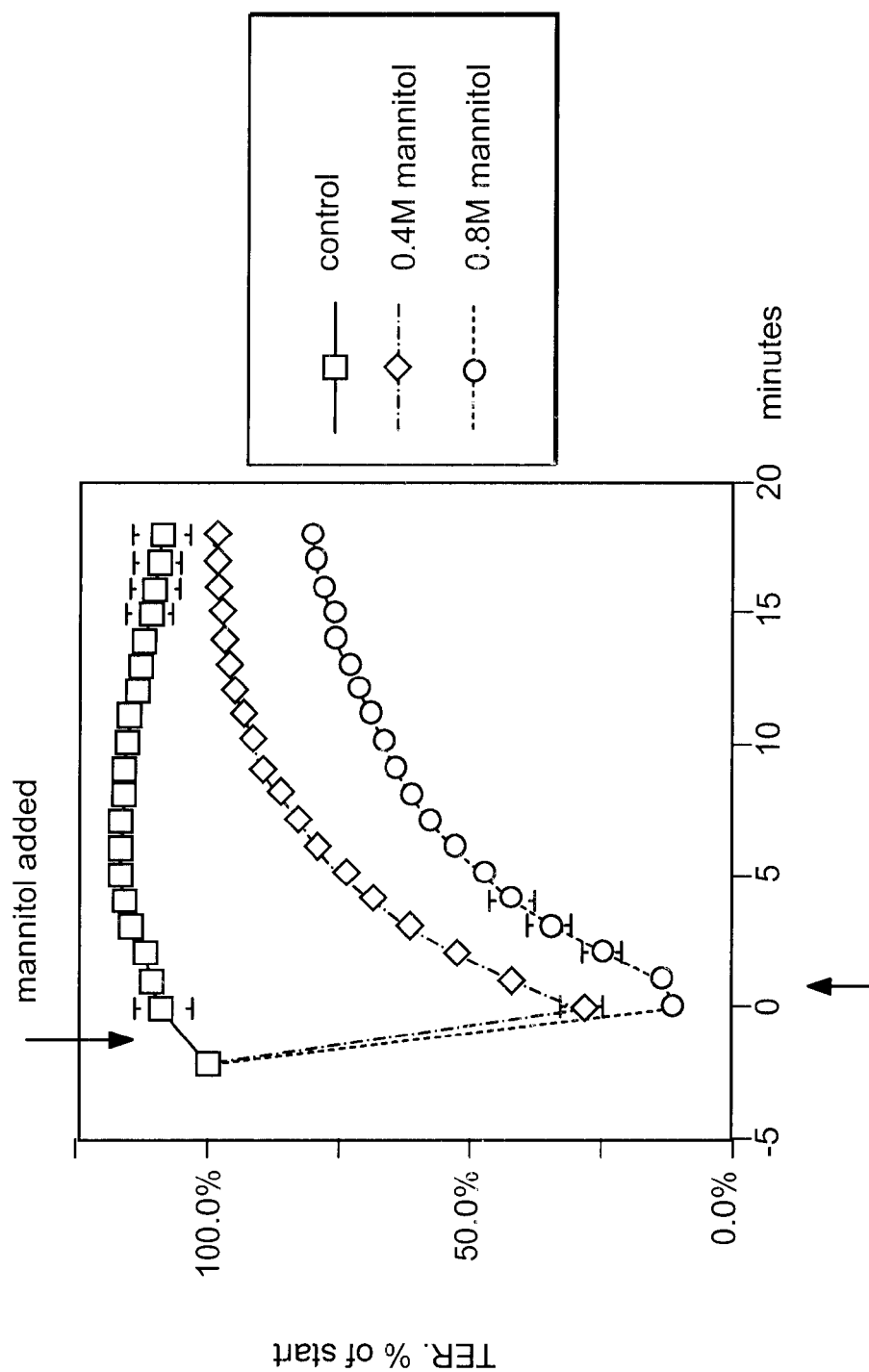
Figure 17A:
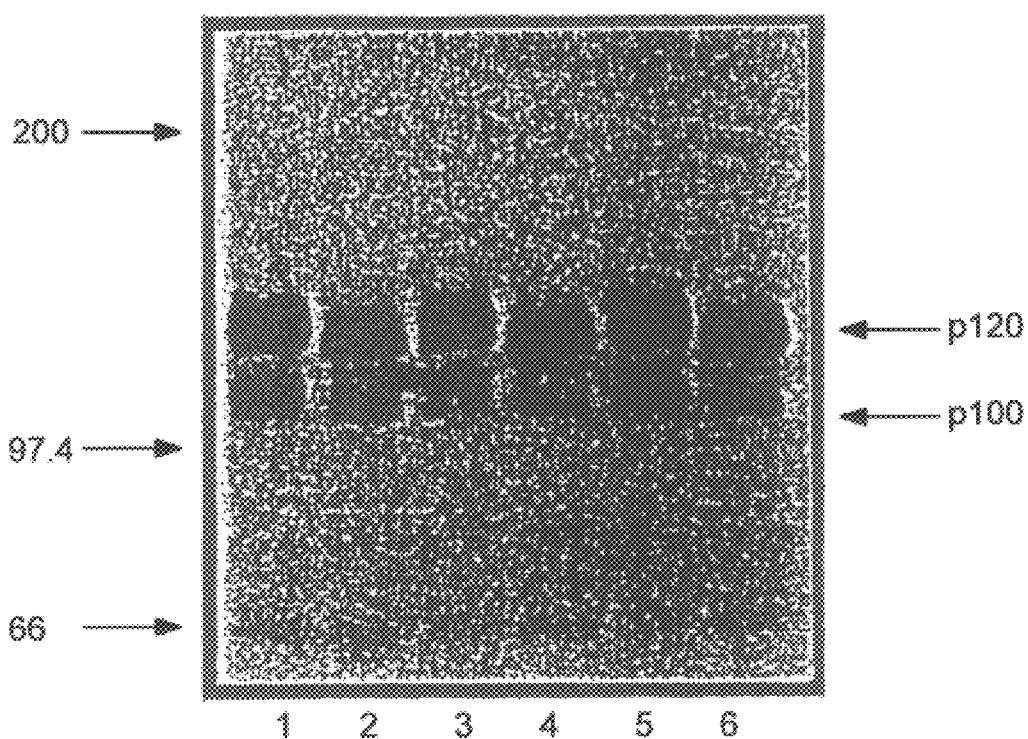
Figure 17B:
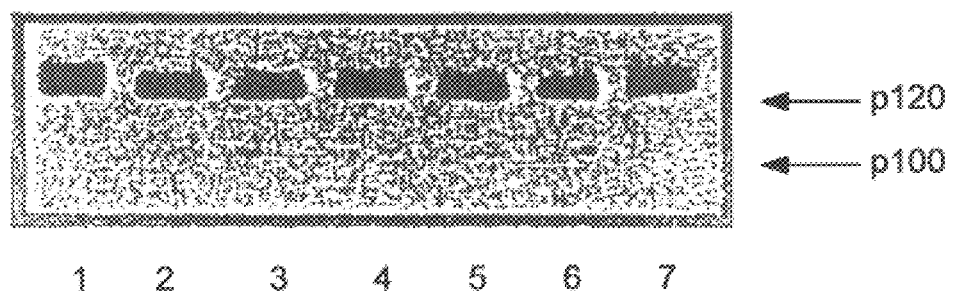
Figure 17C:
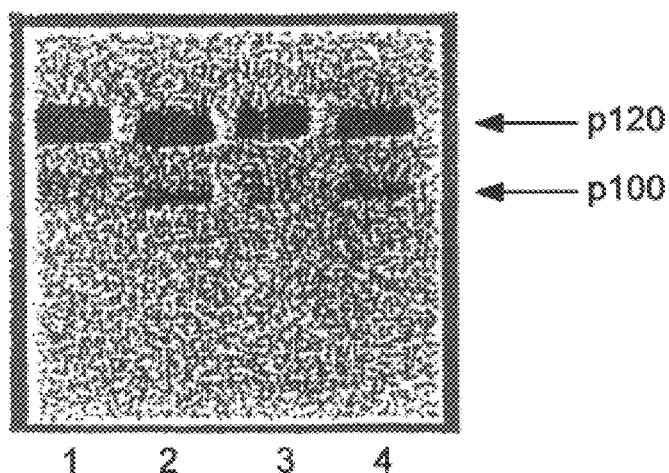
Figure 17D:
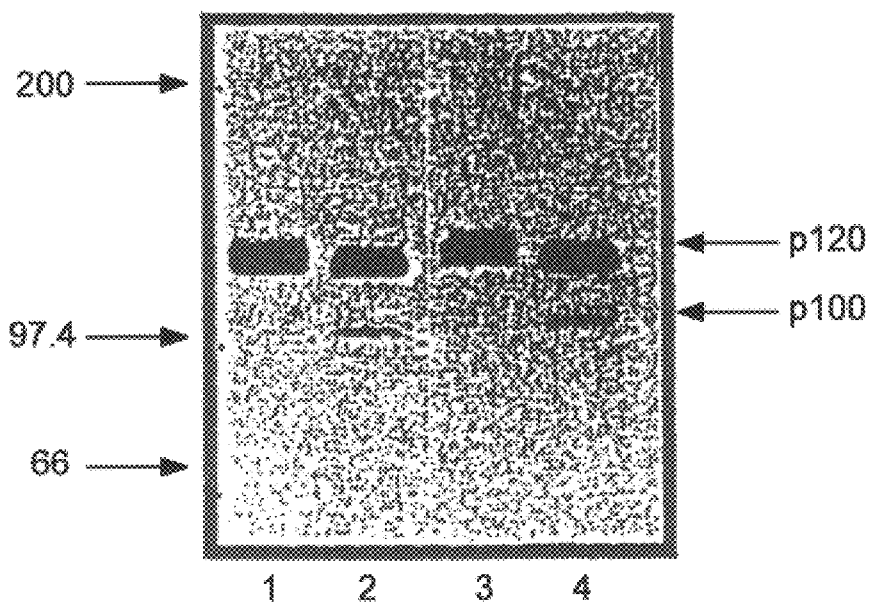

FIGS. 9A and 9B & 9C

It has been shown that although some of the p100/p120 in cells is associated with adherens junctions, there is also a large pool that is not complexed with cadherins (at least by immunoprecipitation analysis). In order to determine which of these p100/p120 pools are subject to dephosphorylation, MDCK I cells were treated with PDB, extracted using Triton lysis buffer, which preserves protein—protein interactions, and immunoprecipitated with E-cadherin antibodies. This procedure served to isolate only that portion of the cellular p100/p120 that associates with the cadherins. Following electrophoresis, and transfer to nitrocellulose, the p100 and p120 present in E-cadherin immunoprecipitates were detected by immunoblotting (Example 9A). It can be seen that the E-cadherin-associated p100/p120 is dephosphorylated in response to PDB. Immunoblot analysis of the non-E-cadherin-associated p100/p120 revealed that this too was subject to dephosphorylation (data not shown). There is no obvious change in the amount of p100 and p120 present in E-cadherin immunoprecipitates after addition of PDB. In addition, immunofluorescence studies in MDCK I cells revealed no change in the localisation of p100 and p120 (Example 9 B, C). Panel (B) shows p100/p120 in control cells, (C) shows p100/p120 in PDB-treated cells (Bar 20 μM). In both cases, p100/p120 is shown to be present at regions of cell—cell contact.

FIG. 10

Human umbilical vein endothelial cells were incubated with histamine (His), pyrilamine (Pyr) or cimetidine (Cim) alone or in combination. As indicated, cells were preincubated in the absence or presence of cimetidine (10 μM) or pyrilamine (10 μM) for 10 minutes and then treated with or without histamine (10 μM) for a further 10 minutes. The cells were extracted and protein analysed by gel electrophoresis and immunoblotting. Histamine alone induced an increased mobility of p100 and p120. Pyrilamine, a $H_1$ blocker, and cimetidine, a $H_2$ block alone had no effect, but pyrilamine blocked the histamine effect. As histamine is an agent well known to be responsible for increased tight junction permeability in endothelial cells, these data raising the possibility that the p100/p120 mobility shift could be causally related to such an increase. The $H_1$-mediated effect of histamine indicates that its effect in some way is mediated by activation of phosphoinosital lipid-specific phospholipase C. Like the effect of phorbol dibutyrate, these data indicate that histamine stimulates dephosphorylation of p100/p120. In the following examples, increase mobility of p100/p120 means decreased phosphorylation.

FIG. 11

Human umbilical vein endothelial cells were incubated with histamine for times indicated. The cells were extracted and protein analyzed by gel electrophoresis and immunoblotting. Histamine induced a rapid increase in the mobility of p100 and p120.

FIG. 12

Human umbilical vein endothelial cells were incubated in the absence (Cont.) or presence of either histamine (10 μM), lysophosphatidic acid (LPA; 10 μM) or ATP (100 μM) for 15 minutes. The cells were extracted and protein analyzed by gel electrophoresis and immunoblotting. Histamine, lysophosphatidic acid and ATP all produce an increase in the mobility of p100 and p120. These diverse agents are know to bind to cell surface receptors to trigger intercellular signalling changes, probably in all cases mediated by activation of phosphoinositol lipid-specific phospholipase C.

FIG. 13

Human umbilical vein endothelial cells were preincubated for 15 minutes with or without the protein kinase C inhibitor bisindolylmaleimide (Bis; 2 μM). The cells were then further treated for 5 minutes with or without histamine (His; 10 μM) or phorbol dibutyrate (PDB; 200 nM). The cells were extracted and protein analyzed by gel electrophoresis and immunoblotting. As before, histamine and phorbol dibutyrate treatment resulted in an increased mobility of p120 and p100. The effect of phorbol dibutyrate was blocked by bisindolylmaleimide, whereas that of histamine was not so strongly affected, suggesting that histamine mainly acts independently of protein kinase C activation.

FIG. 14

Brain endothelial cells from pig were incubated with or without lysophosphatidic acid (LPA; 10 μM for 30 minutes). The cells were extracted and protein analyzed by gel electrophoresis and immunblotting. Each lane represents protein extracted from an individual Transwell. LPA treatment resulted in an increased mobility of p120 and p100. LPA also increases tight junction permeability in these cells (Schulze et al., submitted for publication), raising the possibility that the p100/p120 mobility shift could be causally related to such an increase. Further experiments have shown that the LPA effect on p100/p120 can be seen within a few minutes of addition to the cells.

FIG. 15

Brain endothelial cells from pig were preincubated for 10 minutes with or without the protein kinase C inhibitor bisindolylmaleimide (2.5 μM). The cells were then treated with or without lysophosphatidic acid (LPA; 10 μM for 70 minutes). The cells were extracted and protein analyzed by gel electrophoresis and immunblotting. As before, LPA treatment resulted in an increased mobility of p120 and p100 but this was not blocked by bisindolylmaleimide, suggesting that LPA acts independently of protein kinase C activation. Furthermore, bisindolylmaleimide did not block the ability of lysophosphatidic acid to increase tight junction permeability in these cells (results not shown).

FIGS. 16(A–C)

(a) Hyperosmolar mannitol causes a drop in pig brain endothelial cell transcellular electrical resistance. Pig brain endothelial cell cultures were treated with 0.2–0.4 M mannitol for up to 6 hours and transcellular electrical resistance recorded. The presence of a measurable electrical resistance across a monolayer of cells indicates that there is very little ionic flux across the monolayer, this is only possible when well developed tight junctions are present between cell—cell contacts in the culture. A drop in transcellular electrical resistance represents opening of these cell—cell contacts to ions and the decrease in transcellular electrical resistance in response to hyperosmolar mannitol indicates that hyperosmolarity opens tight junctions. Mean measurements±standard deviation of 3 Transwells are shown. Mean initial transcellular electrical resistance was 815±69 Ωcm² (n=12). (b) The drop in transcellular electrical resistance caused by hyperosmolar mannitol treatment is clearly seen within 20 seconds. Pig brain endothelial cell cultures were treated with 0.8M mannitol and transcellular electrical resistance measurements recorded over 2 minutes. Mean measurements±standard deviation of 3 Transwells are shown. (c) The drop in transcellular electrical resistance caused by hyperosmolar mannitol treatment is fully reversible. Pig brain endothelial cell cultures were treated with 0, 0.4M or 0.8M mannitol. After 2 minutes the Transwells were returned to control medium and transcellular electrical resistance measurements were taken every minute for the following 18 minutes. In another experiment, recovery was also shown to be possible after treatment with 0.8M mannitol for 30 minutes (not shown). Mean measurements±standard deviation of 3 Transwells are shown. Mean initial transcellular electrical resistance was 419±56 Ωcm² (n=9).

FIGS. 17(A–D)

(a) Hyperosmolar mannitol treatment induces an increase in mobility in p100/p120. Pig brain endothelial cell cultures were exposed to 0.4M mannitol for 10 minutes then cells were extracted, protein separated by electrophoresis and p100/p120 detected by immunoblotting. Lanes 1, 3, 5 control cells with iso-osmotic medium; lanes 2, 4, 6 mannitol treated. (b) The increase in mobility in p100/p120 induced by hyperosmolar mannitol is seen within 5 minutes and maintained for 30 minutes. Following hyperosmotic treatment, cells were extracted at the times indicated, protein separated by electrophoresis and p100/p120 detected by immunoblotting. Lane 1; control (no mannitol), lanes 2, 3, 4, 5, 6 and 7: respective 5, 10, 15, 20, 25, 30 minutes treatment with 0.8M mannitol. In a separate experiment the increase in p100/p120 mobility was clearly detected as early as 30 seconds after addition of hyperosmolar mannitol (not shown). (c) The increase in p100/p120 mobility in response to hyperosmolar mannitol is completely reversed 30 minutes after mannitol is removed. Following treatment as indicated, cells were extracted, protein separated by electrophoresis and p100/p120 detected by immunoblotting. Lane 1; no mannitol, lane 2; 5 minutes treatment with 0.8M mannitol, lane 3; 5 minutes in 0.8M mannitol followed 30 minutes recovery in iso-osmotic medium, lane 4; 35 minutes treatment with 0.8M mannitol. (d) The protein kinase C inhibitor bisindolylmaleimide does not alter the pig brain endothelial cell response to hyperosmolar treatment. Hyperosmolar sorbitol was added to pig brain endothelial cell cultures for 10 minutes, causing both a substantial drop in transcellular electrical resistance (from 677 to 73 $\Omega cm^2$) and an increase in mobility of p100/p120. Following pre-incubation with 2.5 $\mu$M bisindolylmaleimide, transcellular electrical resistance dropped to a similar extent (from 643 to 93 $\Omega cm^2$) in response to 10 minutes treatment with 0.3M sorbitol. Likewise, the increase in mobility of p100/p120 in response 0.3M sorbitol was not prevented by inhibition or protein kinase C. Following treatment as indicated, cells were extracted, protein separated by electrophoresis and p100/p120 detected by immunoblotting. Lane 1; control, lane 2; 10 minutes 0.3M sorbitol, lane 3; 15 minutes 2.5 $\mu$M bisindolylmaleimide, lane 4; pretreatment for 5 minutes with 2.5 $\mu$M bisindolylmaleimide followed by addition of 0.3M sorbitol.

MATERIALS AND METHODS

Some but not all of the materials and methods have been described in detail before (see: Rubin et al., 1991: Staddon et al. 1995a,b; Schulze et al., 1997), but those of particular relevance to the present application are described again here.

Chemicals

Phorbol-12,13-dibutyrate (PDB), bisindolylmaleimide I, bisindolylmaleimide V, KT5926, staurosporine (Calbiochem) and 4α-PDB (LC Laboratories), were made up as stock solutions at appropriate concentrations in DMSO, and added to cells at a 1:1000 dilution. $DiC_8$ (Molecular Probes, Inc.) was made up as 50 mM stock in DMSO, and added at 1:100, to give a final concentration of 0.5 mM. Ro 31-8425 was provided by Eisai Ltd. Okadaic acid (Calbiochem) was made up as 100 $\mu$M stock in DMSO, and added at 1:100. Calyculin A (Calbiochem) was made up as 10 $\mu$M stock in PBS, and added to cells at 1:100. In all cases, appropriate vehicle controls were performed.

Cells

MDCK strain I and II cells were provided by Barry Gumbiner (memorial Sloan-Kettering Cancer Center, NY). LLC-PK$_1$ and Caco-2 cells were obtained from the European Collection of Animal Cell Cultures. All cells were maintained at 37° C. under 5% $CO_2$ in humidified air. MDCK strain I and II cells were maintained in MEM containing 10% FCS, 100 U/ml penicillin, 100 $\mu$g/ml streptomycin and 2 mM L-glutamine. Caco-2 cells were maintained in MEM containing 15% FCS, 1% non-essential amino acids and 1 $\mu$g/ml bovine insulin (Sigma I-6634). LLC-PK$_1$ cells were grown in M199 (Gibco), 10% FCS, 100 U/ml penicillin, 100 $\mu$g/ml streptomycin and 2 mM L-glutamine. For whole cell lysate analysis, $10^5$ cells were plated on 6.5 mm diameter, 0.4 $\mu$m, polycarbonate Transwell filters from Costar, in 0.25 ml of medium. The basolateral chamber contained 0.75 ml of medium. For immunoprecipitation, $5 \times 10^5$ cells were plated onto 24 mm Transwell filters, in 2 ml of medium, with 3 ml of medium in the lower chamber. Cells were used 4–7 days after plating.

Tissue culture materials were from Gibco. Porcine brain endothelial cells were isolated and grown by modifications of a previously published procedure (Rubin et al., 1991). Brain capillary fragments were plated on dishes coated with rat tail collagen and human fibronectin. The cultures were fed every other day with growth medium composed of 50% astrocyte-conditioned medium and 50% Dulbecco's Modified Eagle Medium containing 10% plasma-derived serum, 125 $\mu$g/ml heparin, antibiotics and glutamine. They were incubated in a humidified atmosphere of 10% $CO_2$ at 37° C. When the endothelial cells were approximately 50% confluent (after 4–6 days in culture), they were trypsinized and plated onto collagen-coated polycarbonate Transwell filters (6.5 mm diameter, 0.4 $\mu$m pore size, tissue culture treated, Costar Corp, Cambridge, Mass., U.S.A.) in the same medium (250 $\mu$l apically, 750 $\mu$l basolaterally). After 2–3 days on filters, the medium was switched to a 1:1 mixture of astrocyte-conditioned medium and a Dulbecco's Modified Eagle Medium-based, chemically defined medium ('N2', Rubin et al., 1991; Bottenstein and Sato, 1979). The final concentration of plasma-derived serum was 5%. Human umbilical vein endothelial cells were from Clonetics.

Resistance Measurements

Transcellular electrical resistance (TER) measurements were taken with a pair of fixed, current-passing, voltage measuring electrodes (World Precision Instruments, Stevenage, Hertfordshire, U.K.). TER values are expressed in $\Omega cm^2$ and were corrected for the resistance of cell-free filters.

Cell Lysis and Immunoprecipitation

Whole cell lysates were prepared by rapidly replacing the culture medium in 6.5 mm with hot Laemmli sample buffer, followed by heating at 100° C. for 5 minutes. Immunoprecipitations were carried out at 4° C. Confluent monolayers of cells were washed rapidly with ice cold PBS (containing 0.9 mM $CaCl_2$ and 0.5 mM $MgCl_2$) before addition of 0.5 ml of the appropriate buffer. The filters were then gently scraped, and the lysate was removed and centrifuged at 14000× g. The supernatant was precleared with 10% (w/v) protein A-Sepharose in lysis buffer for 30–60 minutes. Appropriate primary antibodies were added to the lysate, and after 2–3 hours the immunecomplex was isolated, using rabbit anti-mouse secondary antibodies (Jackson Immunoresearch Labs Inc., West Grove, Pa.) and protein A-Sepharose. The beads were washed fives times with lysis buffer, and the bound protein was solubilized in SDS-sample buffer, followed by heating at 100° C. for 5 minutes.

For Immunoprecipitations, Triton lysis buffer or TDS lysis buffer was used. Triton lysis buffer (pH adjusted to 7.4 using NaOH) contained 25 mM Hepes, 1% Triton X-100, 2 mM EDTA, 0.1 M NaCl, 25 mM NaF, 1 mM vanadate, and protease inhibitors. TDS lysis buffer (pH 7.4) comprised Triton lysis buffer supplemented with 0.5% sodium deoxycholate and 0.2% SDS. The protease inhibitors used in each case were; leupeptin, 10 $\mu$g/ml; α2-macroglobulin, 0.1 U/ml; soybean trypsin inhibitor, 10 $\mu$g/ml and PMSF, 1 mM. Antibodies recognising E-cadherin, β-catenin and p120 were obtained from Transduction Labs. (Lexington, Ky.).

Electrophoresis and Immunoblotting

Cell extracts or immunoprecipitates in SDS sample buffer were resolved by SDS-PAGE. The slab gels were then equilibrated in buffer comprising; 48 mM Tris, 39 mM glycine, 20% methanol and 0.03% SDS. Proteins were transferred to nitrocellulose filters (Hybond ECL; Amersham), which were Ponceau S stained and then blocked for 2 hours at 37° C. with 1% BSA in PBS containing 0.05% Tween-20. Filters were then probed with p120 antibody, at a dilution of 1:2500. After washing, filters were incubated with horseradish peroxidase conjugated anti-mouse antibody (Amersham), at a dilution of 1:5000. The filters were then extensively washed in PBS/0.5% Tween-20, and immunoreactive bands were detected by enhanced chemiluminescence (Amersham) following the manufacturers instructions.

Phosphate Labelling

MDCK I cells grown to confluence on 24 mm filters were incubated overnight in phosphate-free MEM, containing 0.5% serum (dialysed against 0.9% NaCl and 10 mM Hepes (pH 7.5)) and 100 $\mu$Ci/ml [$^{32}$P]orthophosphate (Amersham). Cells were treated with 200 nM PDB for 30 minutes, then lysed into TDS buffer, and immunoprecipitated with p120 antibodies as described above. Following transfer of proteins to nitrocellulose, the filters were exposed overnight to film, and the resulting autoradiograph of [$^{32}$P]-labelling scanned by densitometry using a Bio-Rad Imaging Densitometer GS-670. Filters were then probed with p120 antibodies, and the resulting ECL exposure scanned in the same way, to quantify protein loading.

For phosphoamino acid (PAA) analysis, MDCK I cells were labelled as above with [$^{32}$P]orthophosphate, and the p100 and p120 extracted from PDB-treated or untreated cells by immunoprecipitation (as above). Following transfer to Immobilon P, and immunoblotting to assess recovery of protein, the area of the filter containing p100 and p120 was excised. The proteins were hydrolysed at 110° C. for one hour in 5.7 M HCl to release PAAs. Following lyophilisation, two dimensional PAA separation and detection was carried out as previously described (Boyle et al., 1991).

Immunofluorescence Staining

Cells were fixed at room temperature for 20 minutes in 3% paraformaldehyde made up in PBS containing 0.5 mM CaCl$_2$ and 0.5 mM MgSO$_4$. Fixed cells were washed and then permeabilized by incubation with 0.5% Triton X-100 in PBS for 10 minutes. After washing, the cells were incubated for 30 minutes in PBS containing 10% calf serum and 0.1 M lysine, pH 7.4. Incubation with p120 antibody (0.5 $\mu$g/ml) was in PBS containing 10% calf serum for 1 hour. After washing, the cells were then incubated for 60 minutes with a 1:100 dilution of FITC-conjugated anti-mouse IgG (Jackson Immunoresearch Labs), in PBS containing 10% calf serum. After washing, the filters were mounted with Citifluor (Citifluor Products, Canterbury, UK) and examined using a Nikon Microphot-FXA fluorescence microscope fitted with 40× and 60× objectives. Photographs were taken using Kodak T-Max film (400 ASA).

REFERENCES

Boyle W J, Van der Geer P and Hunter T., Phosphopeptide Mapping and Phosphoamino acid Analysis by Two-Dimensional Separation on Thin-Layer Cellulose Plates. Methods in Enzymology 1991: 201: 110–149.

Laemmli UK cleavage of structural proteins during the assembly of the head of bacteriophage T4. Nature (London) 1970: 227: 680–685.

Schulze C, Smales C, Rubin L L and Staddon J M. Lysophosphatidic acid increases light junction permeability in brain endothelial cells. Journal of Neurochemistry 1997: 68: 991–1000.

Staddon J. M., Herrenknecht K., Smales C., and Rubin L. L., Evidence that tyrosine phosphorylation may increase tight junction permeability. Journal of Cell Science 1995a: 108: 609–619.

Staddon J. M., Smales C., Schulze C., Esch F. S., and Rubin L. L., p120, a p120-related protein (p100), and the cadherin/catenin complex. Journal of Cell Biology 1995b: 130: 369–381.

Rubin L. L., Hall D. E., Porter S., Barbu K., Cannon H. C., Horner H. C., Janatpour M., Liaw C. W., Manning K., Morales K., Tanner L. I., Tomaselli K. J., and Bard F. A. cell culture model of the blood-brain barrier. Journal of Cell Biology 1991: 115: 1725–1735.

What is claimed is:

1. A method of modifying the permeability of a physiological barrier comprising modifying the phosphorylation of serine or threonine residues of p100 and/or p120, by either (a) inducing the phosphorylation of serine and/or threonine residue of p100 and/or p120 with an agent capable of inducing the phosphorylation of serine and/or threonine residue of p100 and/or p120 to decrease the permeability of physiological barriers, or (b) inducing the dephosphorylation of phosphorylated serine and/or threonine residues of p100 and/or p120 with an agent capable of inducing the dephosphorylation of phosphorylated serine and/or threonine to increase the permeability of physiological barriers.

2. The method of claim 1, wherein in (a) the agent capable of inducing the phosphorylation is a protein kinase C inhibitor.

3. The method of claim 2, wherein the protein kinase C inhibitor is selected from the group consisting of N-(2-aminoethyl)-5-chloronaphthalene-1-sulfonamide, bisindolylmaleimide I, chelerythrine chloride, Gö6976, Gö7874, 1-(5-isoquinolinesulfonyl)-2-methylpiperazine, hypericin, K-252a, K-252c, K-252c, melittin, phloretin, pseudohypericin, rottlerin, Ro 31-8220, Ro 32-0432, LY 333531, and (–)balanol.

4. The method of claim 1, wherein in (b) the agent capable of inducing the dephosphorylation is a protein kinase C activator.

5. The method of claim 4, wherein the protein kinase C activator is selected from the group consisting of phorbol diesters, bryostatin 1, bryostatin 2, (–)indolactams V, (+)indolactam V, teleocidind, 6-(N-decylamino)-4-hydroxymethylindole, 3-(N-acetylamino)-5-(N-decyl-N-methylamino)benzyl alcohol, lipotoxin A4, lipotoxin B4, mezerein, (–)-7-octylindolactam V, resiniferatoxin, and thymeleatoxin.

6. The method of claim 4, wherein the protein kinase C activator is a ligand that binds to a receptor to generate diacylglycerol.

7. The method of claim 6, wherein the ligand is a neuropeptide.

8. The method of claim 7, wherein the neuropeptide is bombesin.

9. The method of claim 6, wherein the ligand is platelet-derived growth factor or epidermal growth factor.

10. The method of claim 1, wherein in (a) the agent binds lysophosphatidic acid or histamine.

11. The method of claim 1, wherein in (b) the agent is lysophosphatidic acid or histamine.

12. A method to decrease the permeability of the blood-brain barrier comprising administering an agent capable of inducing the phosphorylation of serine and/or threonine residue of p100 and/or p120.

13. The method of claim 12, wherein the agent is administered to prevent damage to the brain following passage of a drug across the blood-brain barrier.

14. The method of claim 12, wherein the agent is administered to block or reduce the entry into the brain of lymphocytes which mediate an immune response.

15. The method of claim 12, wherein the agent is administered to prevent or reduce the entry of metastatic cancer cells into the brain.

16. The method of claim 12, wherein the agent is administered to prevent or reduce the risk of brain oedema following stroke or traumatic head injury.

17. A method to increase cell—cell adhesion comprising administering an agent capable of inducing the phosphorylation of serine and/or threonine residue of p100 and/or p120.

18. A method to increase the permeability of a physiological barrier comprising administering an agent capable of inducing the dephosphorylation of phosphorylated serine and/or threonine residue of p100 and/or p120.

19. The method of claim 18, wherein the agent is administered to allow a drug to pass across the blood-brain barrier.

20. The method of claim 18, wherein the agent is administered to open pulmonary epithelial cell tight junctions.

21. The method of claim 18, wherein the agent is administered to treat disorders in which mucous accumulates in the lungs.

22. The method of claim 18, wherein the agent is administered to aid in the administration of a drug to the lungs.

23. The method of claim 18, wherein the agent is administered to aid in the administration of a substance useful in diagnosis to reach a desired location.

24. The method of claim 23, wherein the desired location is the brain.

\* \* \* \* \*